United States Patent [19]

Houwen et al.

[11] Patent Number: 5,519,214

[45] Date of Patent: May 21, 1996

[54] METHOD FOR ANALYSIS OF DRILLING FLUIDS

[75] Inventors: Otto Houwen, Cambridge, England; Alan Gilmour, Port Harcourt, Nigeria; Mark Sanders, Kincardinshire, Scotland

[73] Assignee: Schlumberger Technology Corporation, Sugar Land, Tex.

[21] Appl. No.: 295,734

[22] PCT Filed: Feb. 26, 1993

[86] PCT No.: PCT/GB93/00406

§ 371 Date: Jan. 9, 1995

§ 102(e) Date: Jan. 9, 1995

[87] PCT Pub. No.: WO93/17326

PCT Pub. Date: Sept. 2, 1993

[30] Foreign Application Priority Data

Feb. 29, 1992 [GB] United Kingdom ............ 9204407

[51] Int. Cl.$^6$ ............ G01N 23/22; E21B 49/00

[52] U.S. Cl. ............ 250/256; 378/45

[58] Field of Search ............ 250/256; 78/45, 78/46, 50, 90, 88

[56] References Cited

U.S. PATENT DOCUMENTS 3,848,881 10/1974 Barton, Jr. et al. ............ 378/88
3,858,037 12/1974 Moore et al. ............ 378/88
4,510,573 4/1985 Boyce et al. ............ 378/48

*Primary Examiner*—Davis L. Willis
*Assistant Examiner*—Richard Hanig
*Attorney, Agent, or Firm*—Peter Y. Lee; Wayne I. Kanak

[57] ABSTRACT

A method of analyzing a drilling fluid comprising subjecting a sample of the fluid to an XRF analysis technique and comparing the results obtained with a calibration model to determine the amount of one or more components of the fluid present in the sample. The method is particularly useful for determining solids in the fluid such as barite and can be combined with an FTIR technique which is sensitive to other components of the fluid. A PLS algorithm is used to construct the model from the spectra.

25 Claims, 17 Drawing Sheets

CALCIUM CALIBRATION

METHOD FOR ANALYSIS OF DRILLING FLUIDS

BACKGROUND OF THE INVENTION

1. Field of the Invention

The present invention relates to a method of analysing drilling fluids and is particularly useful for the determination of solids in drilling fluids and differentiation between the different types of these solids.

2. Description of the Related Art

During the drilling of an oil or gas well, large volumes of solids cuttings are generated by the drill bit. These solids are conveyed to the surface by means of circulating drilling fluids, often known as "mud", which are often complicated mixtures of water, oil, soluble and insoluble minerals, polymers, surfactants and salts. A large portion of the drill cuttings can usually be removed from the fluid by means of vibrating screens and other solids separators, so that after this cleaning process the fluid can be recirculated down the drill string. However, some of the drill cuttings are dispersed as very small particles, which cannot be removed by the solids separation process. The presence of these fines, often called "drilled solids" (DS), affects the functional properties of the fluid. Determination of the concentration of DS is particularly complicated by the presence of two other types of solids in the fluid, commercial clays and weighting material.

Commercial clays are added to the fluid for control of rheological and filtration properties. Usually, bentonite or other chemically treated clay minerals are added for this purpose. The total of commercial clays (CC) and DS is called "low gravity solids" (LGS).

Weighting materials are used to bring the fluid to the required density, necessary to contain underground formation fluids by hydrostatic pressure exerted by the mud column in the annulus. A common weighting material is powdered barite (barium sulfate). The concentration of weighting materials is known as "high gravity solids" (HGS).

It is important for effective control of the properties of the fluid to know the individual concentrations of all types of solids. In current well site technology LGS and HGS are not measured directly, but are calculated from the density and solids volume fraction of the drilling fluid, both of which can be measured. The principle of the calculation is that both properties are functions of the volume fractions of LGS and HGS. A simple form of these functions is assumed, and from the resulting set of two simultaneous equations with two unknowns one can readily solve LGS and HGS. This is usually done by direct calculation or by the use of charts which may allow for corrections if salts are present.

The total concentration of clays can conveniently be determined at the well site from their ability to absorb certain cationic dyes. This is the basis for the well-known methylene blue test, which provides a value known as "MBT value" for the concentration of chemically active clays. The larger part of these clays comes usually from the intentionally added commercial clays, the remainder is derived from clay minerals in the drilled solid fraction. If an average proportion of chemically active clays in the drilled solids is assumed, then it is possible to calculate DS and CC from LGS and MBT.

As mentioned, previously proposed techniques for the determination of individual solids concentrations relies on the direct measurement of density and solids volume fraction of the fluid. Density is measured with a "mud balance", a well-known rig site device. Solids volume fraction is measured by evaporation of a fluid sample of known volume in an electrically heated distillation apparatus, also well-known as the "mud retort". The liquid distillate is collected in a graduated receiver, and from the volume of distillate and the volume of the original fluid sample the volume fraction of total solids is calculated. Problems associated with the use of these two pieces of equipment are the possibility of an incorrect apparent density as determined by the mud balance because of the presence of gas in the fluid sample, and further, the fact that the mud retort suffers from errors caused by leaks in the vapour condenser and the inability to accurately introduce a known sample volume. Further errors are also caused by the assumptions enabling solution of the simultaneous equations mentioned previously. In this respect a density for the weighting material needs to be assumed. In the case of barite, drilling grade material is in fact a mixture of pure $BaSO_4$ (specific gravity 4.5) and impurities. The commercial product has specific gravity 4.20–4.25 at best. Furthermore, the specific gravity of the drilled solids are known with even less certainty. Corrections need to be applied if oil or soluble salts are present in the fluid. These corrections are also based on measurements with limited reliability and on not precisely known physical properties. Because on the large number of measurements and questionable assumptions made in the current methods, the resulting values for DS and HGS are known to be of limited value. It is, for example, not unusual to find negative numbers for the concentration of barite, or to find unreasonably high values for the drilled solids content.

Control of the composition has been recognised as important in maintaining the desired properties of the drilling fluid and various methods have been proposed for monitoring the composition of the drilling fluid. The ionic composition of the fluid can be analysed using ion chromatography and this can also be used to obtain an indication of the cation exchange capacity of the clay materials present. Examples of this are found in our copending patents and applications U.S. Pat. No. 4,904,603, U.S. Pat. No. 4,878,382 and EP 89203062.8 which are incorporated herein by reference. It has also been found that a more complete analysis, including information on both organic and inorganic and mineral composition can be obtained using FFIR. Examples of this can be found in our copending European and UK patent applications EP 90202796.0, EP 90202795.2, and UK 9107041.7 also incorporated herein by reference. However, all of these methods encounter some problem when attempting to determine the amount of solids in a sample, particularly if the size of the solid particles interferes with the measurements.

SUMMARY OF THE INVENTION

It is an object of the present invention to provide a method for analysing drilling fluids which allows improved measurement of the solid material contained therein.

The object of the invention is achieved using an X-ray fluorescence (XRF) analysis technique. Although such techniques are well known for general chemical analysis and have even been proposed for the analysis of core samples taken from wellbores (see GB 2,225,110), no such technique is known to exist which enables the accurate determination of the composition of drilling fluids.

In EP-A-0067514, which is considered particularly useful for a quantitative borehole analysis of surrounding rock, concentrations of chemical elements are determined by detecting from the object examined both an XRF-signal of an element in question and a Compton scattering signal. The analysis of the element follows in essence from a curve-fitting of the ratio of those signals to known element concentrations in calibration objects.

According to CA-A-1219688 a potential ore block is irradiated with gamma radiation. The resulting X-ray fluorescence and Compton scattering are detected, and these two signals are compared with each other, their ratio reflecting the heavy metal content in the block. Rejection of the block takes place on the basis of the X-ray fluorescence signal to Compton signal ratio, and therefore their ore potential, falling below a threshold value.

In accordance with the broadest aspect of the present invention, there is provided a method of analysing a drilling fluid comprising solids suspended in a liquid phase, the method comprising subjecting a sample of the fluid to an X ray fluorescence analysis technique so as to derive a spectrum therefrom; analysing the spectrum to identify a peak of intensity $I_{HGS}$ in the spectrum due to the presence of a component of the high gravity solids fraction of the sample and a peak of intensity $I_{Co}$ due to Compton scattering and determining the ratio $I_{HGS}/I_{Co}$; and using data from the derived spectrum, the ratio $I_{HGS}/I_{Co}$ and a calibration model to calculate the amount of said component and liquid phase in the sample.

The advantage of using an XRF technique is that it is particularly sensitive to the minerals which comprise the high gravity solids present in drilling fluids, especially barite. The XRF spectrum will also contain some features which are due to components of the fluid which do not themselves have an XRF spectrum but which affect the spectrum of those components which do. Consequently, by preparation of a suitable calibration model it is possible to calculate properties of the fluid such as water content, oil and brine content and specific gravity. If the specific gravity of the sample is measured, this can be used to improve the calculation of the content of the components of the fluid, oil/water ratio, brine density etc. Likewise, the amount of LGS in the sample can be calculated despite the fact that very little of the LGS produces an XRF spectrum of its own.

Determination of the ratio $I_{HGS}/I_{Co}$ is important since the component peak and the Compton scattering peak both contain information relating to the average atomic number Z of the sample which can be calculated from the ratio of the two. It is preferred that the method involves irradiating the sample with radiation which provides a strong signal due to the presence of barium or, if any other weighting material is present, a constituent of the weighting material. It has been found particularly advantageous to monitor the $L_\alpha$ and $L_{k\alpha}$ lines of the barium spectrum when determining the concentration of barite.

The determination of the concentration of barium in whole mud samples is linked through the simple chemical constitution of barite to the concentration of HGS in the mud. Hence, having an accurate measurement of HGS constitutes an improvement over the conventional techniques for mud solids measurement, which rely on the retort and the mud balance and, as described before, require the determination of two unknowns, HGS and LGS, from a set of two simultaneous equations. For example, LGS can be found from:

$$LGS=1.667\ W-1.296\ HGS-1.667$$

where LGS and HGS are concentrations in g/L, and W is the mud density in kg/L. HGS is now the concentration of barite, directly determined according to the invention although it will be appreciated that other relationships might also be used.

In a further aspect of the present invention, there is provided a method of determining the concentration of polymer in drilling fluids comprising analysing the mineral concentrations in a sample by XRF and using the thus determined mineral concentrations to calibrate the IR spectrum of the sample with respect to the mineral components and analysing said spectrum with respect to the polymers.

Measurement of organic components in mud by FTIR, typically using the PLS technique is often difficult because they are present in small quantities. The spectra are dominated by mineral components which are usually present in larger quantities yet calibration is hampered by the fact that the minerals often do not have well deemed spectra as they have a variable, mixed composition, as witnessed for example by the large number of clay minerals occurring in sediments. The application of this aspect of the invention consists of determining at least barite by XRF and importing this information, as non-spectral information, into a suitable FTIR calibration model. In the case of weighted muds, this information would determine to some extent the composition of the mud, and one source of uncertainty is removed from the input data set. As a result the prediction of trace components, such as organics is improved. A further extension of this idea is to input the Ca-LGS and non-Ca-LGS as determined by XRF as weB. Again this should help in resolving some of the difficulties experienced by the PLS algorithm caused by ill-defined FTIR spectral features.

A single element technique based upon measurement of the intensity of the barium fluorescence line or lines is potentially applicable to the present invention. In the case of typical drilling mud formulations the concentrations of barite can be sufficiently high to cause significant non-linearity of the curve relating barium fluorescence intensity to barite concentration. As concentrations of barite increase, self absorption of the fluorescence by barium becomes more important, until the fluorescence signal saturates. However, in practical drilling mud formulations, saturation is not reached over the range of possible barium concentrations. In addition to self absorption, attenuation and scattering of the fluorescence radiation by the matrix plays also a role. This matrix effect can generally be corrected for in quantitative XRF spectrometry if analyte concentrations are low and the matrix has a known density or composition. Under these conditions count rate $I_{Ba}$ of the fluorescence peak for barite is proportional to barium concentration [Ba]:

$$I_{Ba}=s[Ba]$$

The sensitivity of the measurement, s, is inversely proportional to the mass absorption coefficient $\mu/\rho$:

$$s=\frac{K_1}{\mu/\rho}$$

where $\mu/\rho$ itself is roughly proportional to the third power of the average atomic number Z:

$$\mu/\rho=K_2 Z^3$$

Hence, one finds that the barium count rate is strongly dependent on $Z^3$:

$$I_{Ba} = \frac{K_1}{K_2} \frac{[Ba]}{Z^3}$$

The basis for a number of conventional algorithms consists of relaxing this strong matrix dependency by division of the barium count rate by a background count rate, which is approximately inversely proportional to $Z^2$. It is convenient to take for the background reading the area of the Compton scattering (incoherent scattering peak), $I_{Co}$, so that $$I_{Co} = \frac{K_3}{Z^2}$$

which leads to $$[Ba] = \frac{I_{Ba}}{I_{Co}} Z \frac{K_2 K_3}{K_1} = \frac{I_{Ba}}{I_{Co}} Z K_4 = X Z K_4$$

where X is the ratio between barium fluorescence and Compton scattering count rates.

At concentrations of barium that are common in mud engineering, this linear relation between X and [Ba] breaks down and can be replaced by, for example, a power series such as:

$$[Ba] = b_0 + b_1 X + b_2 X^2 + b_3 X^3$$

or by a hyperbolic function such as $$[Ba] = \frac{A + I_{Ba}}{B + C I_{Co}}$$

In both examples the empirical coefficients $b_0$, etc. and A,B,C are determined from calibration samples containing known amounts of barium. In this empirical approach an attempt is made to use Compton scattering, which has been shown to be inversely proportional to the mass absorption coefficient, as a means to eliminate the matrix effect; using the same symbols as before one have $$I_{Co} = K_2 K_3 \frac{Z}{\mu/\rho}$$

The potential problem with the single element method is that empirical calibration methods based on the relationship $$[Ba] = \frac{I_{Ba}}{I_{Co}} Z K_4$$

will have only limited success if Z varies from sample to sample and is not known.

A fundamental problem in mud engineering is that the matrix of drilling mud samples is variable as a result of contamination with formation minerals and the presence in unknown amounts of mud chemicals. Thus, some of the elements other than barium that may be present in appreciable variable quantities are S, Cl, K and Ca., and also Cr and other transition metals. This means that the average Z, which influences the relation between [Ba] and the count ratio X, is unknown. The consequences of this uncertainty can cause errors when muds containing the interferences were measured using calibration coefficients derived from calibration sets of muds not containing the interference. To circumvent the matrix problem, a large number of calibrations could be made from which one would be selected on the basis of chemical knowledge of the sample, for example the calcium content. However, care must be taken to avoid undesirable degrees of complication, arbitrariness, and operator dependency. It is also difficult to achieve one single calibration model to describe a wide range of barite concentrations, so that overlapping calibration models can be avoided. When using the empirical correlations such as (power series) and (hyperbolic relation), there often remains some curvature of a plot of actual versus predicted concentrations.

In one method which could overcome the problem of variable Z is to input Z (average atomic number of the sample) with the calibration samples as a non spectral attribute in a PLS regression technique. This would create a calibration model ("PLS+Z") where the Z is necessary as an input, along with the XRF data. The measurement of an unknown would then go in two stages. In the first stage one measures it with a calibration model that does not require Z ("PLS w/o Z"). This would give an approximate value for the elements Cl, K, Ca, Ba, from which one reconstructs the average chemical composition of the sample, from which Z is computed. In the second stage the spectral data plus the just calculated Z is input into the "PLS+Z" model and a better accuracy should result. The process may need to be reiterated to converge on constant composition.

Frequent recalibration is required to compensate for machine drift, which requires large numbers of calibration samples. Thus, in order to obtain sufficiently accurate values for the calibration coefficients $b_i$ in the power series equation, typically about 10 calibration samples have to be presented to the analyser and the coefficients calculated by a regression technique e.g. PLS. The input data used in this calibration process and also in the subsequent determination of barite in unknowns is the ratio X, determined from pre-set windows spanning the barium fluorescence and Compton scatter peaks. Ideally the calibration sample set should consist of simulated muds, in order to let the analyser see the correct matrix. But it is impractical to store mud samples for the longer times required, as they require frequent mixing to avoid settling of a thin barite layer on the bottom of the sample cells, which would completely distort the analysis. Hence the samples need to be stored in separate stirred containers and poured out into the sample cells before calibration. This makes the technique in field practice prone to errors (caused for example by unintended cross contamination between samples). Alternatively solids samples could be constructed from barite and some fixation agent (glass, resin, etc.). The problem with this solution is the different matrix, which precludes use of the Compton peak. Finally, a durable solid reference sample could be used to restandardise the analyser before measurement of unknowns, but over periods of months sufficient line broadening of the barium fluorescence occurs to invalidate earlier calibrations, since the Compton peak does not change in time at the same rate as the fluorescence peak, and therefore the ratio X is not constant in time. Thus, the single element approach via empirical correlations described above can have practical drawbacks when used on a drilling rig.

A solution to practical problems associated with the single element technique described above is to use more spectral information in addition to the spectrum produced from a single source (usually Am 241), and to use the information from all individual channels of a multichannel analyser. With this technique barite can be determined with greatly improved accuracy compared with the single element methods studied.

There is also sufficient information to calculate LGS, SG, etc. and for this purpose one uses a second source, such as Fe 55, typically with a sealed Ne/CH4 detector. This source allows K line fluorescence peaks to be observed from S, Cl, K, Ca, Cr, and the L-α peak from Ba. All of these peaks overlap. Since calibration of this system would be very complicated, a regression technique is utilised, Partial Least Squares (PLS), developed by Wold et al. Suitable windows in the spectral data are selected and the PLS calibration technique is presented with spectral data from a large set of calibration muds. To obtain acceptable accuracy it is necessary to do some preprocessing of the spectral data by means of expressions similar to the ratio $I_{Ba}/I_{Co}$, discussed above. Generally, individual channels are used instead of summations of channels. The PLS technique requires large numbers of calibration samples, depending on the number of components in the samples.

It is advantageous to use two sources which have different responses to the components of the mud under analysis. In the case described above, the Am 241 source provides a signal which can be used to obtain an indication of the Ba content of the sample. Ba also contributes to the signal from the Fe 55 source and so the estimation of the Fe 55 signal contribution from Ba can be improved by inputting the Am 241 estimation of the Ba content into the PLS algorithm as applied to the Fe 55 signal. This in turn improves the estimation of the other mud components from the Fe 55 signal since the Am 241 Ba estimation is in effect an internal calibration for that sample. Thus the output from the PLS analysis of the signals from both sources provides an estimation of Ba, Ca, K, Cl, LGS, $H_2O$, specific gravity (SG) and average atomic number (Z). The estimate of SG and Z can then be taken and applied to PLS analysis of the same data as non-spectral attributes which will allow improved estimation of Ba, Ca and K. In an alternative case, SG is measured separately and is input into the PLS algorithm as a non-spectral attribute which will improve the measurements further but does require an extra measurement.

The time taken for that preparation and measurement of the calibration samples is often such that appreciable drift of the analyser can take place during the calibration phase. This is potentially a severe limitation to accuracy achieved when the calibration is used at a later stage to determine concentrations of unknowns. It is therefore essential to correct for any a drift in the calibration and measurement procedure.

Analyser drift is caused by decay of the source and is significant only for an Fe 55 source. More important is drift of the sealed detectors, which is a combination of two ageing phenomena. In the first a gradual decay of count rates is noted in which the output from each channel of the multi-channel analyser decreases over time when standard samples are measured. The second phenomenon is deterioration of resolution, which is noted as peak spreading. As a result of peak spreading the rate by which individual channels decrease their output depends on the significance they have for the analysis. For example, the barium fluorescence peaks present in the Am 241 spectrum are quite sharp. The maxima of these peaks decrease in time, but the fringes rise. Hence to correct for drift in this spectral region, each channel of the unknown sample needs to be multiplied by a different appropriate correction factor which is determined from measurement of a suitable standard sample. Alternatively all channels covering the peaks concerned could be summed, but this would in time cause some of the peaks' energy to spread beyond the boundaries of the summation interval. It has also been found that the accuracy of measurement improved by treating individual channels separately. As described here the drift correction procedure serves to guarantee continuity between the time a calibration model is constructed and the time an unknown sample is analysed.

A second practical advantage of drift correction is that it allows one calibration model to be transferred between different analysers. Because of the ageing process, the detectors will generally exhibit a different degree of resolution. By measurement of suitable standard samples the appropriate correction factors for individual channels can be found, allowing a calibration model to be used that was constructed on a different analyser.

A third use of drift measurements is provision of a warning mechanism for unusual conditions of the analyser. The decay characteristics of the detector performance were found to obey an exponential decay law. Occasionally individual measurements on standard samples can be well outside the statistically expected range, and this could be correlated by events such as periods of idleness of the analyser, transportation, or climatic differences. The system needed then to adjust to changed conditions and during the adjustment period discrepancies could occur between measurements made shortly after each other.

BRIEF DESCRIPTION OF THE DRAWINGS

The present invention will be described by way of example, with reference to the accompanying drawings, in which.

DESCRIPTION OF THE PREFERRED EMBODIMENT

EXAMPLES

Figure 1:
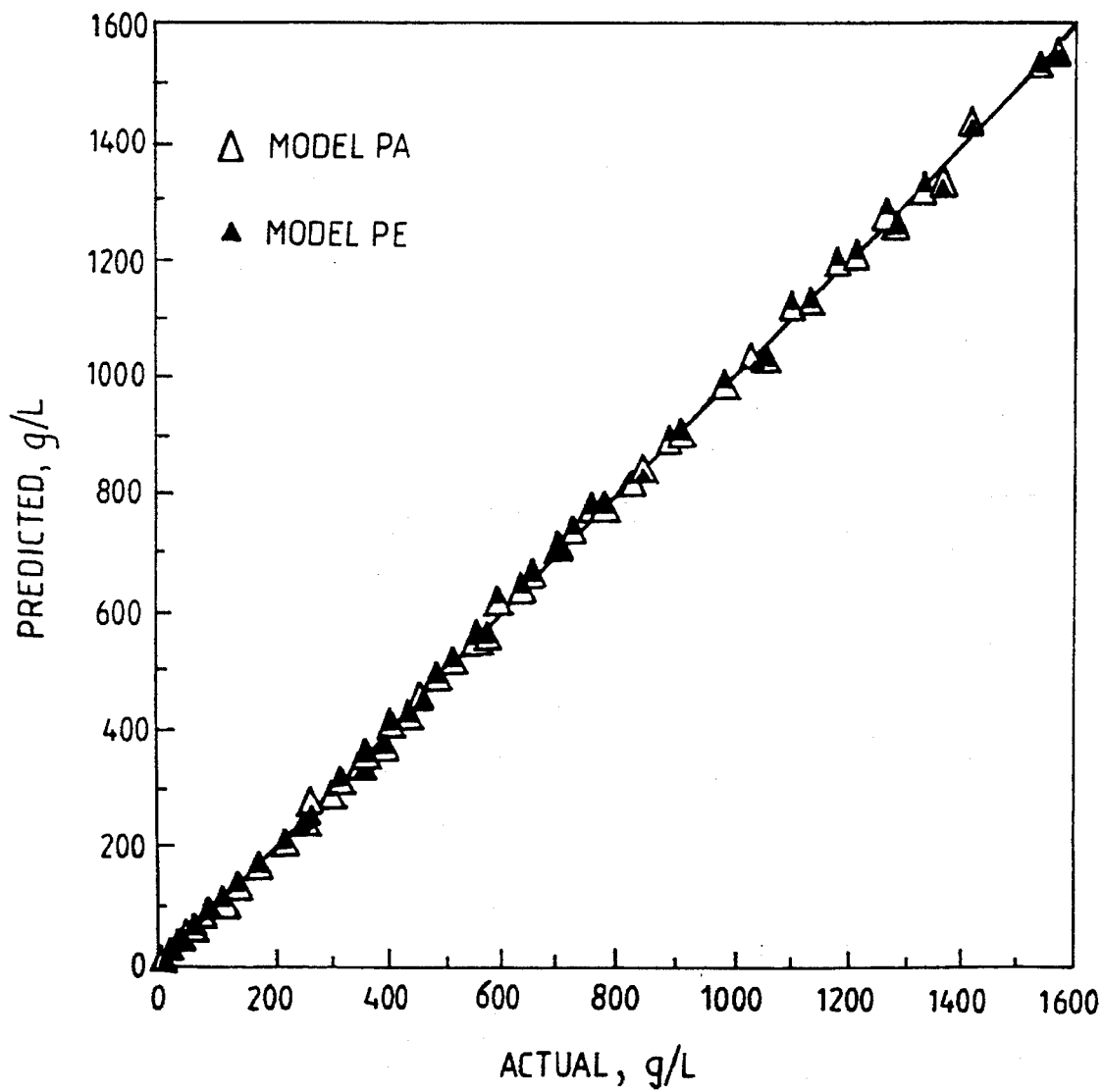
FIGS. 1–16 show plots for calibration and validation of a model to interpret the results of the method according to the present invention.
Figure 2:
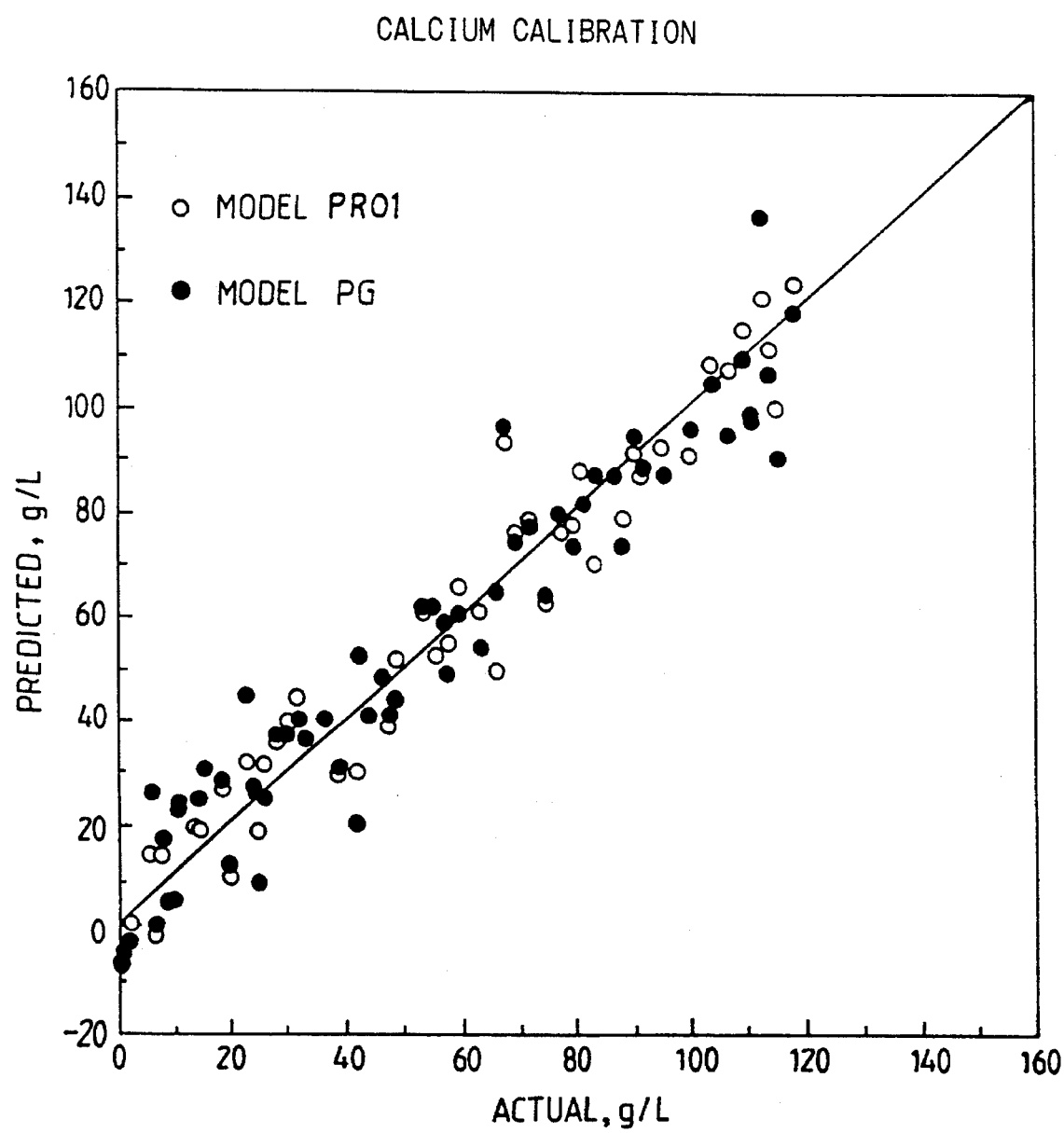
Figure 3:
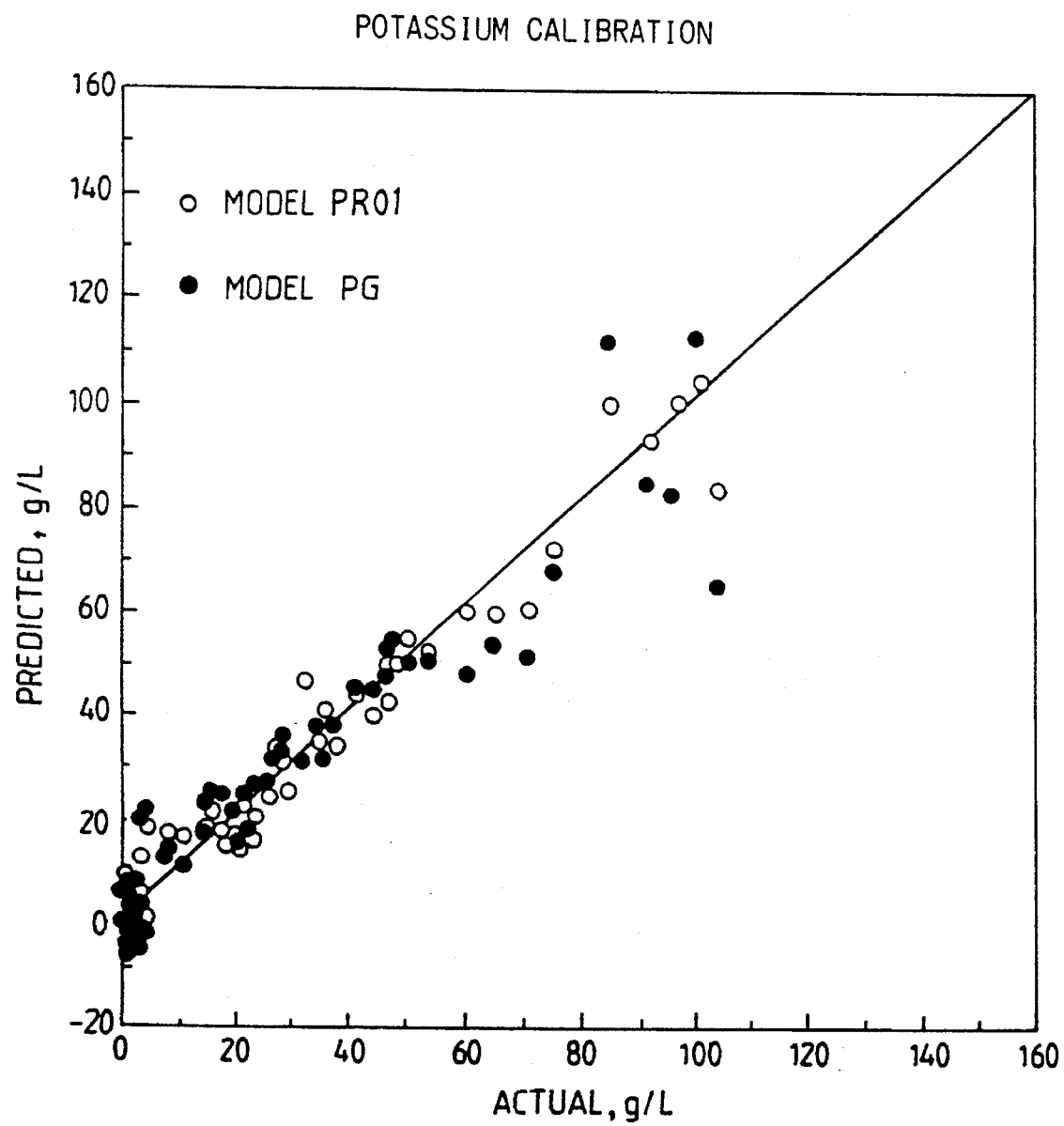
Figure 4:
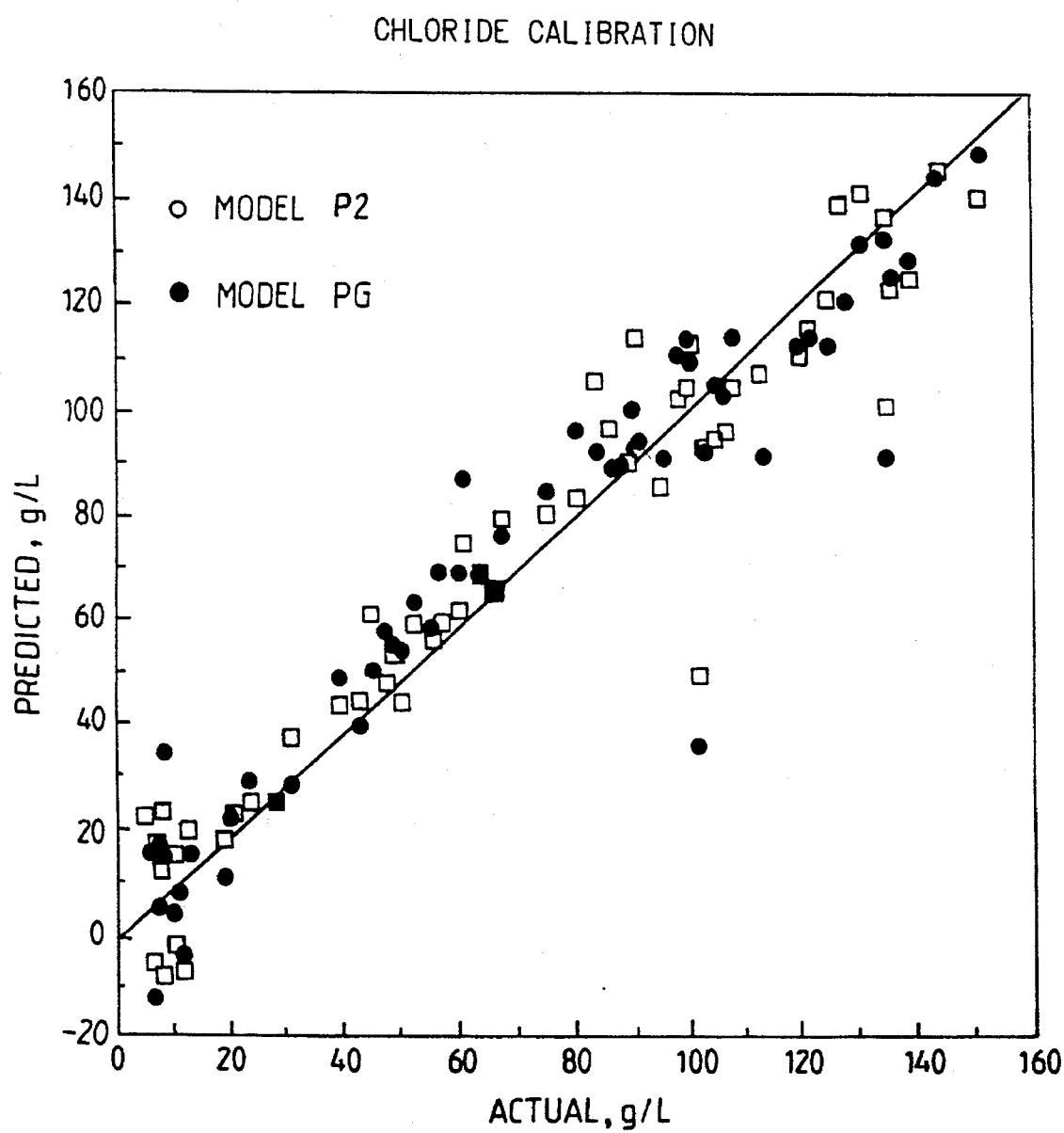
Figure 5:
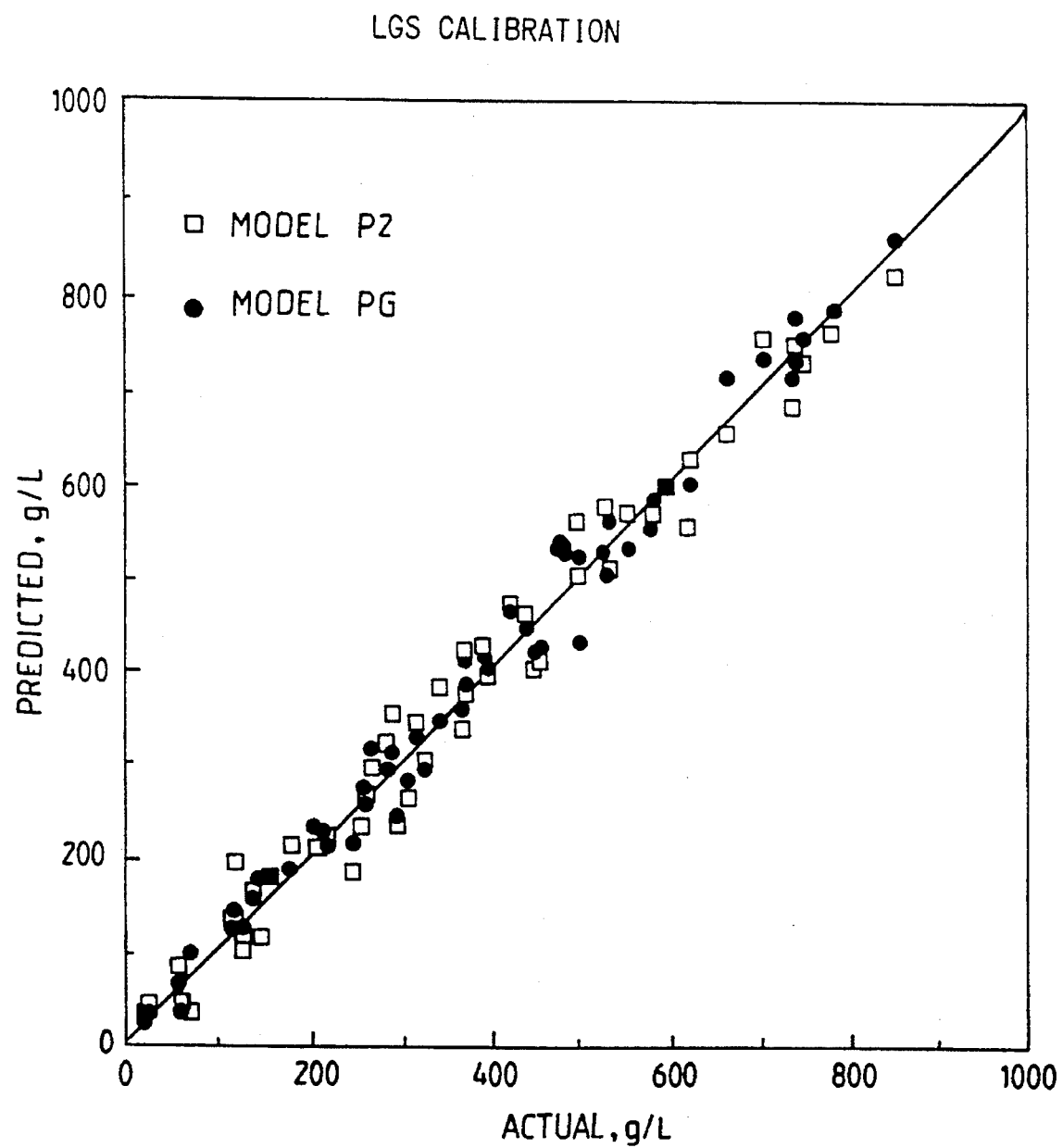
Figure 6:
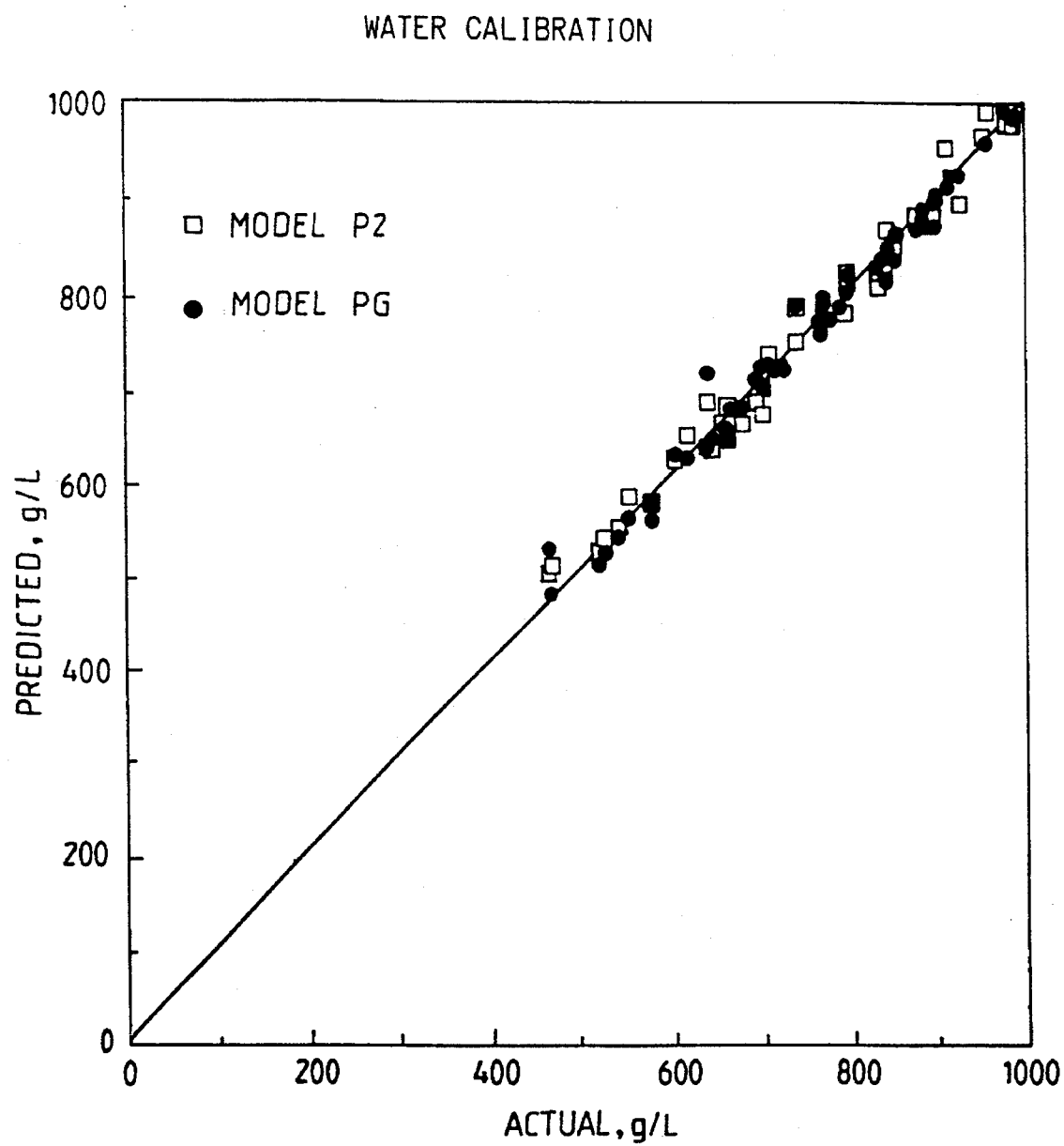
Figure 7:
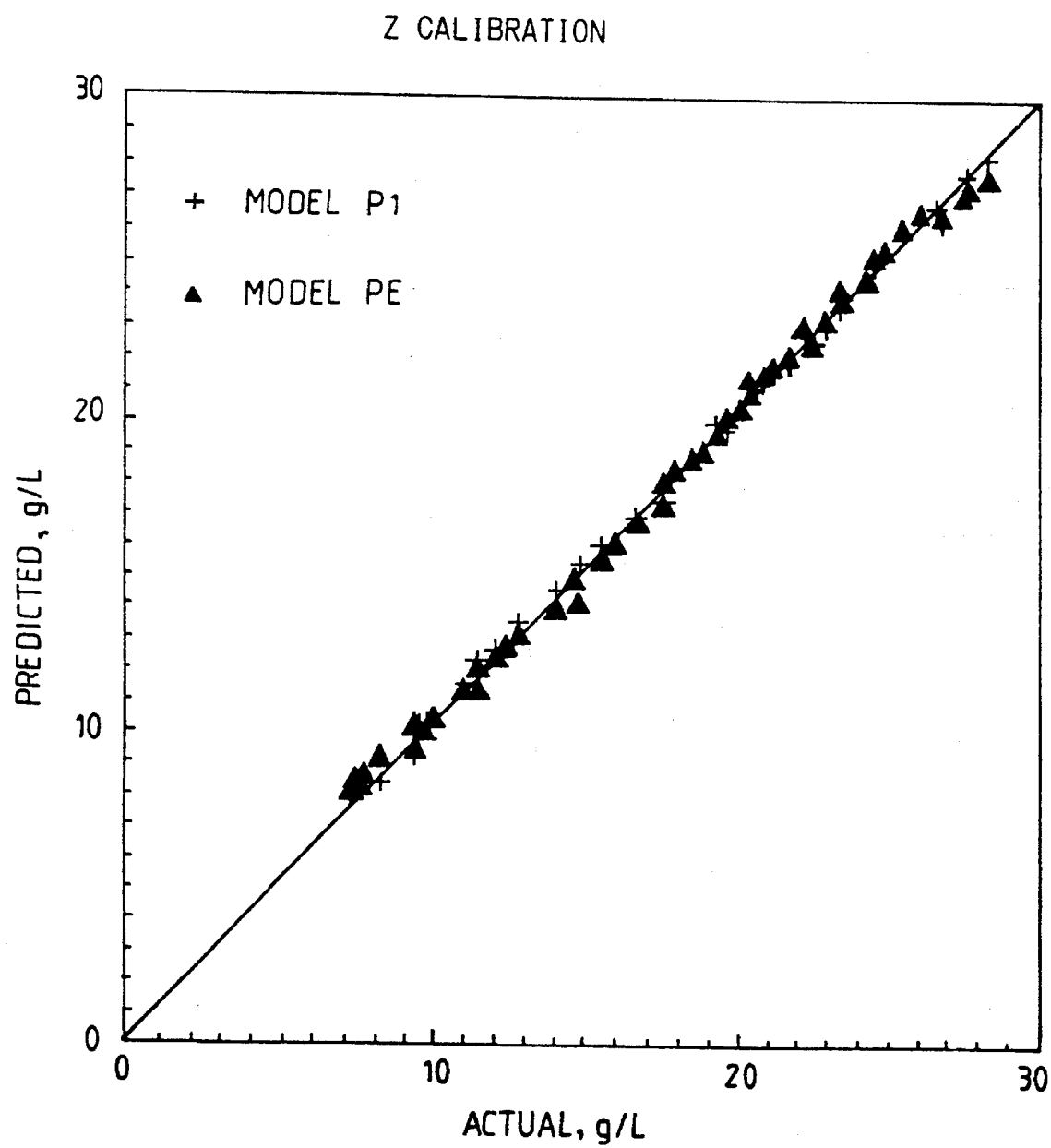
Figure 8:
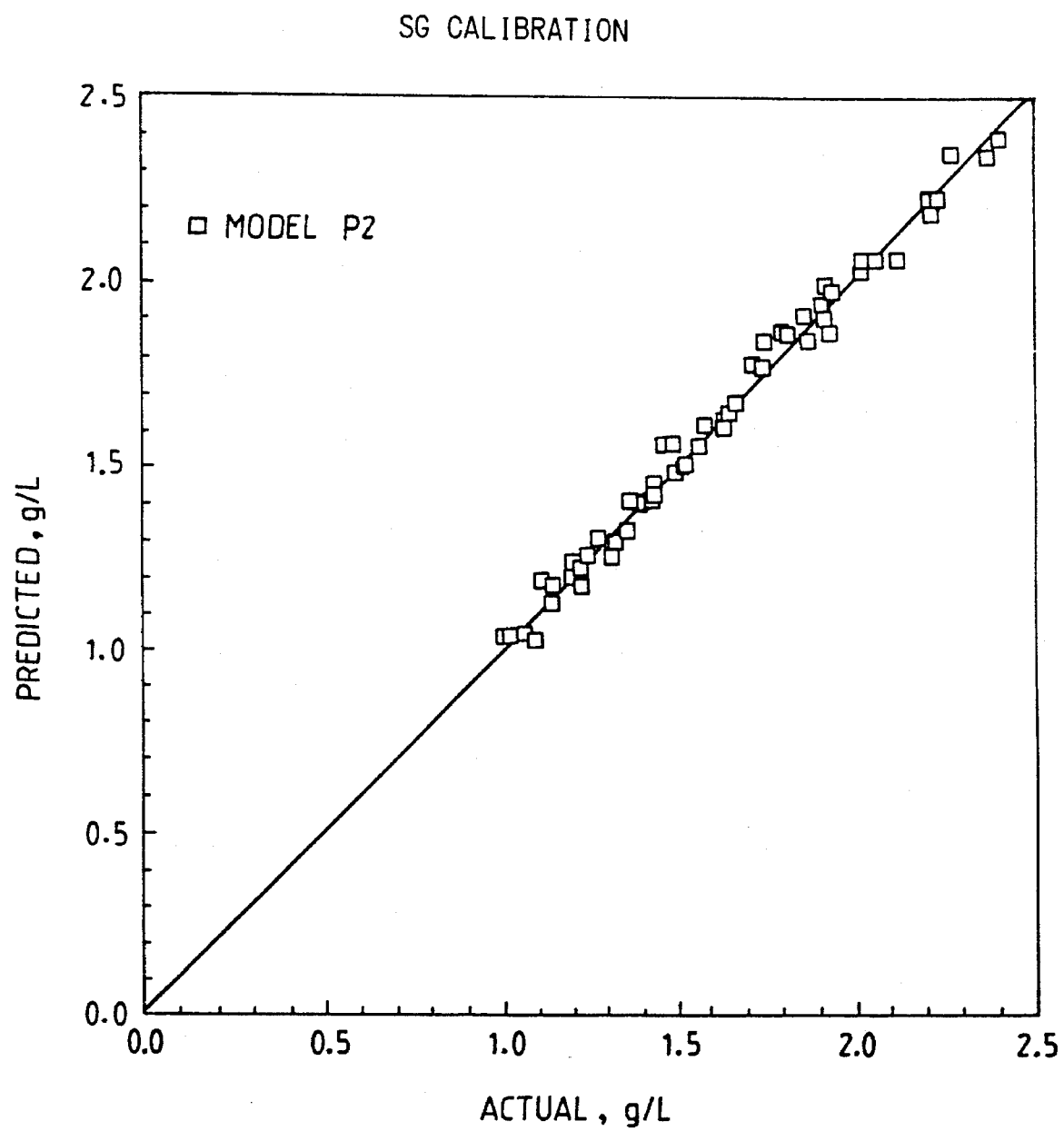
Figure 9:
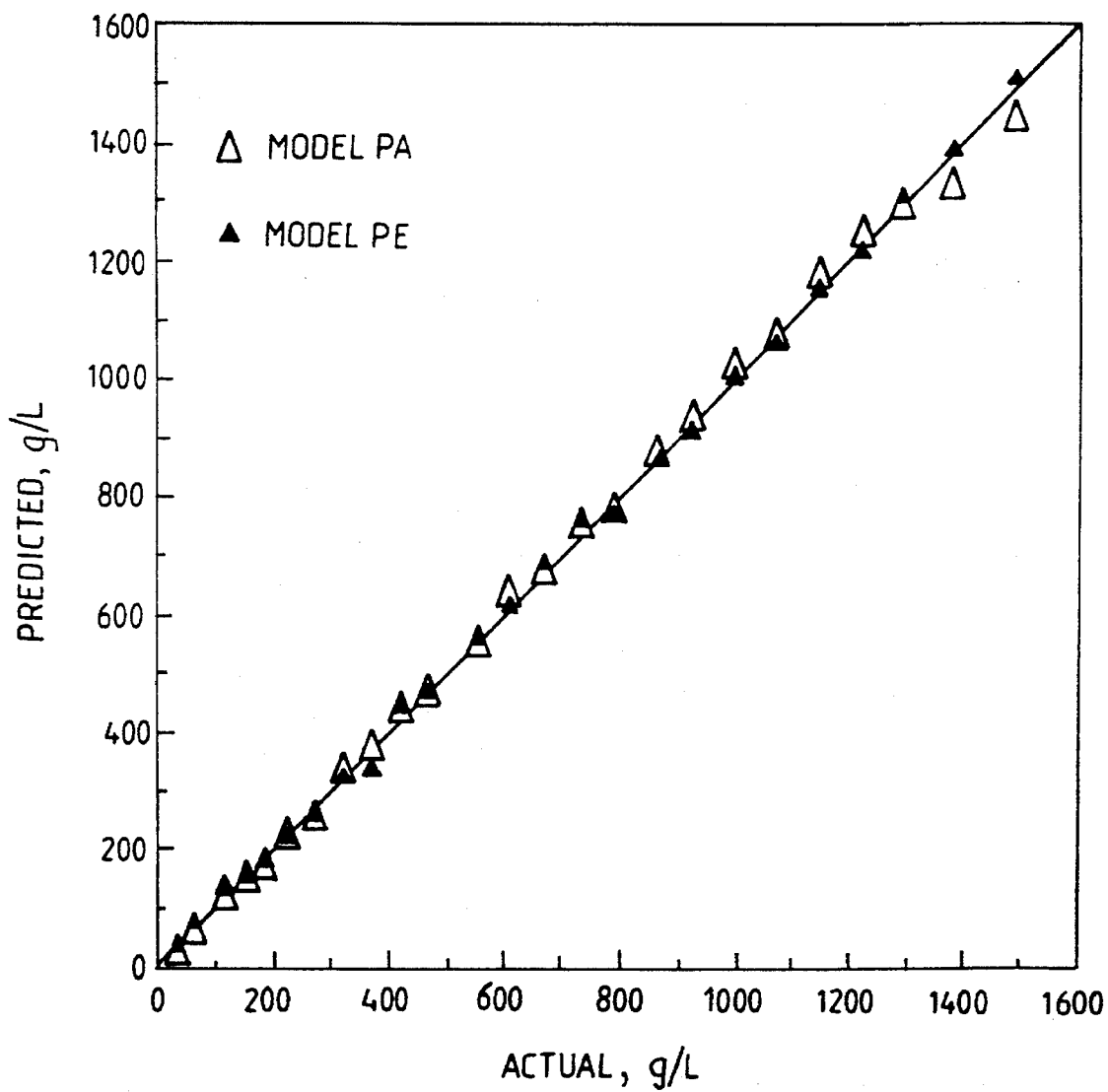
Figure 10:
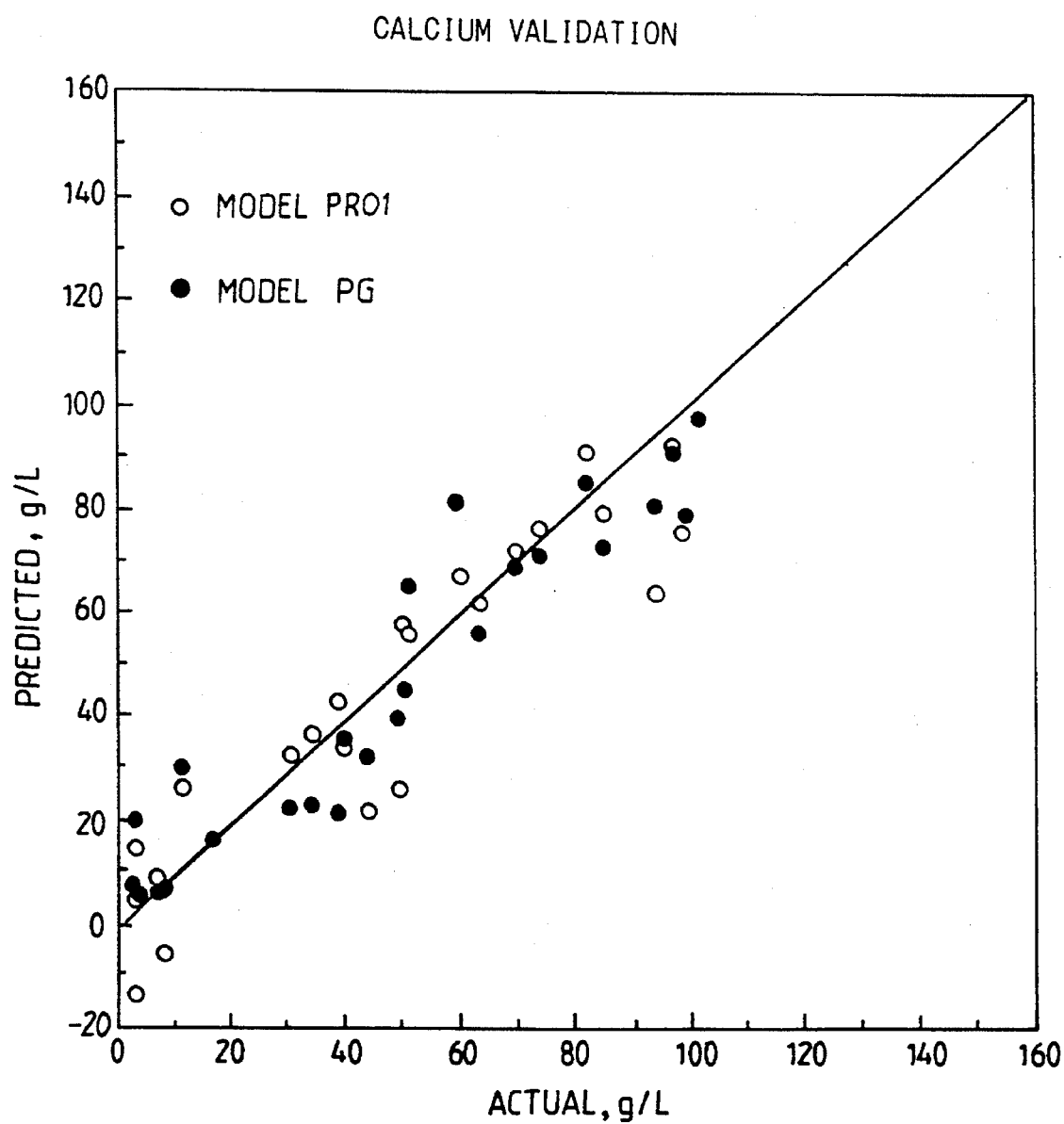
Figure 11:
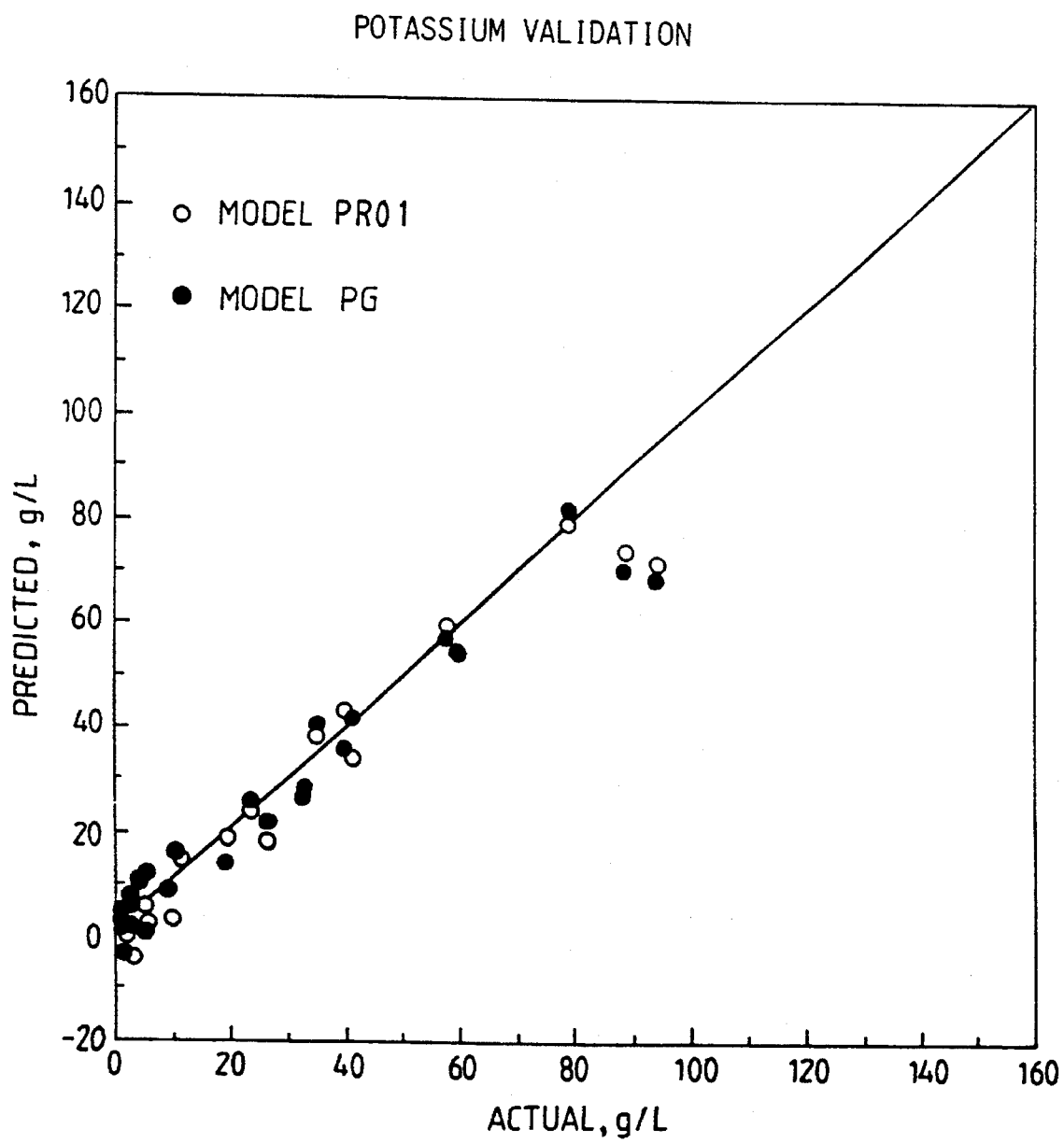
Figure 12:
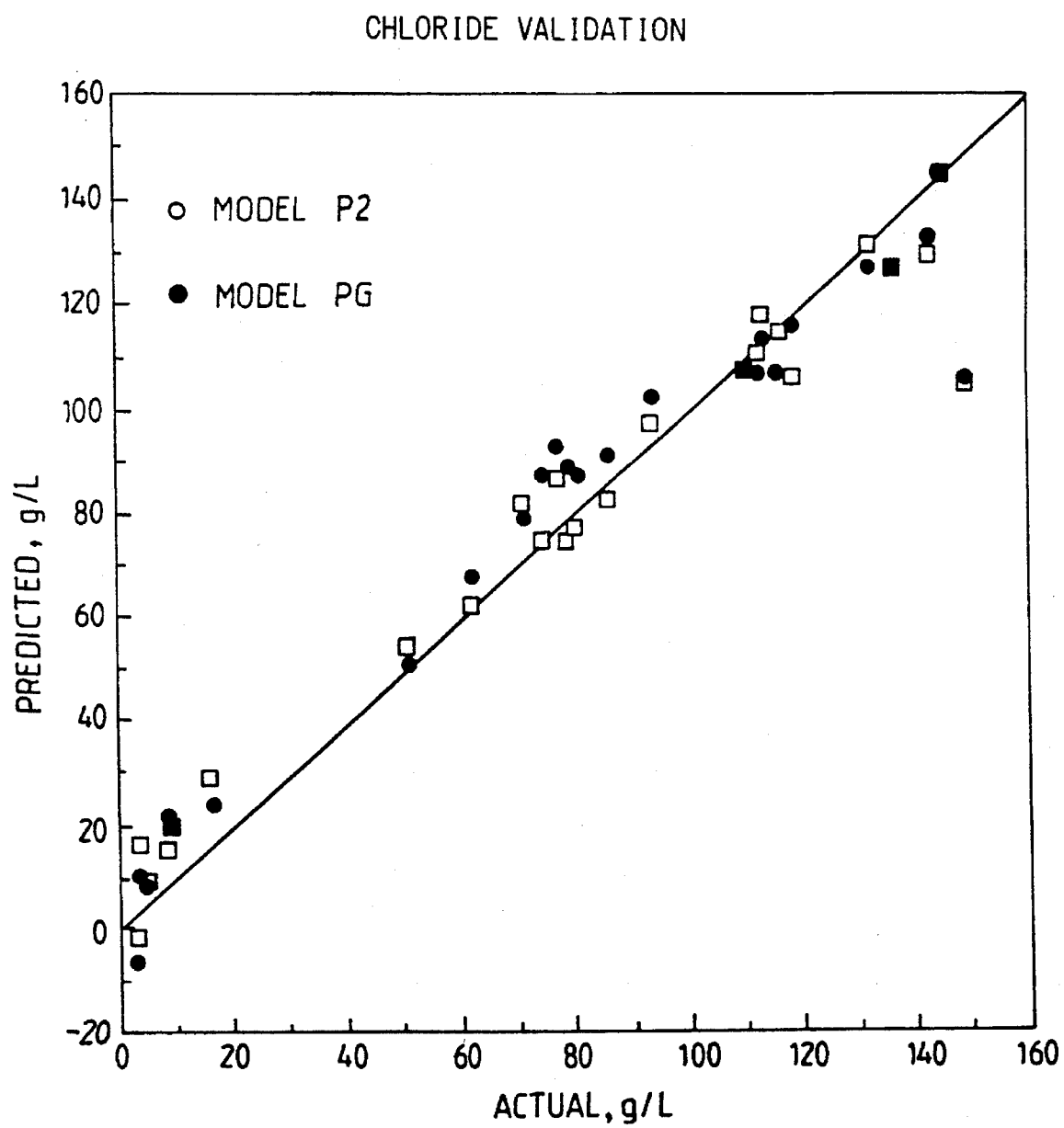
Figure 13:
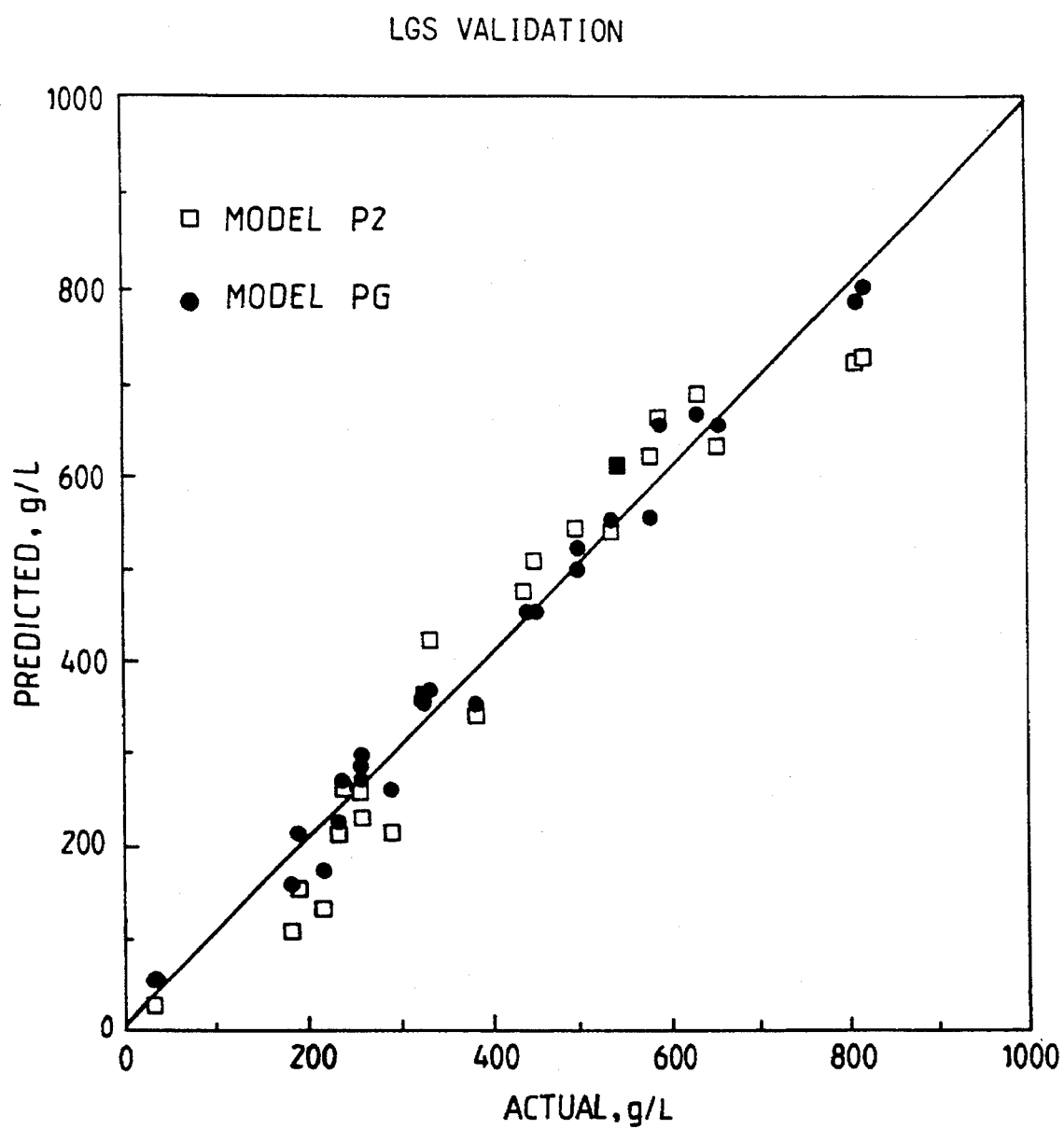
Figure 14:
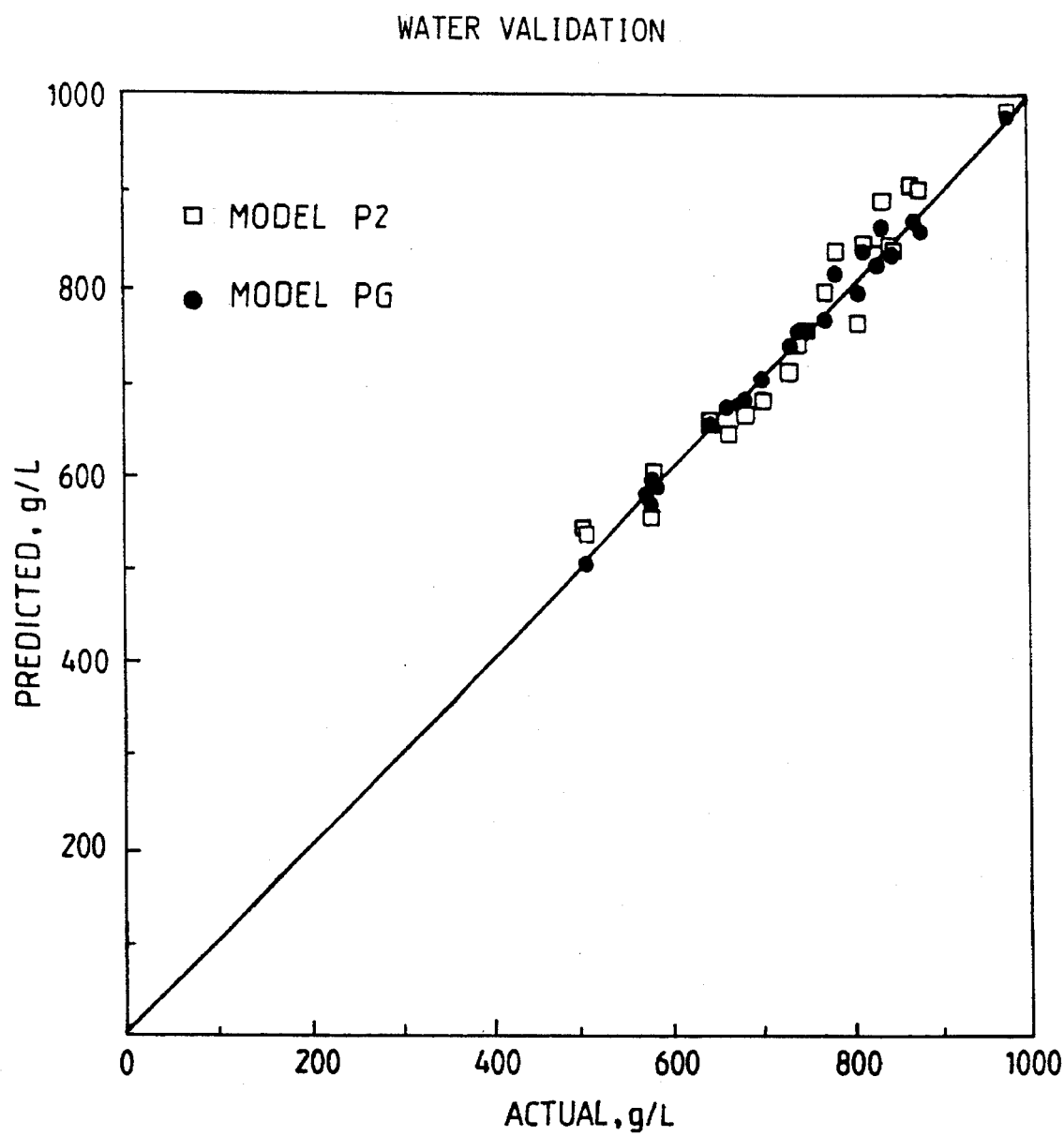
Figure 15:
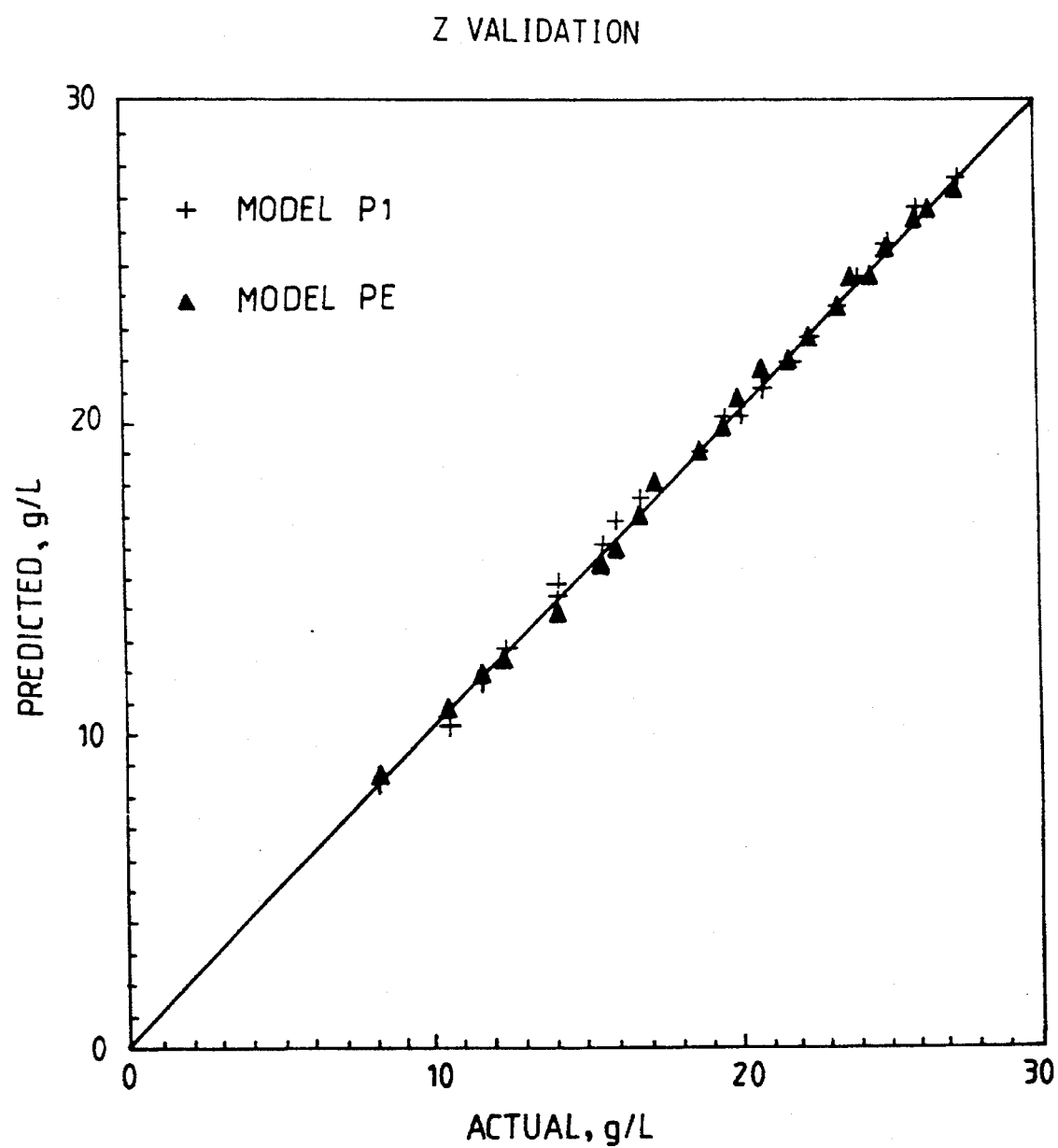
Figure 16:
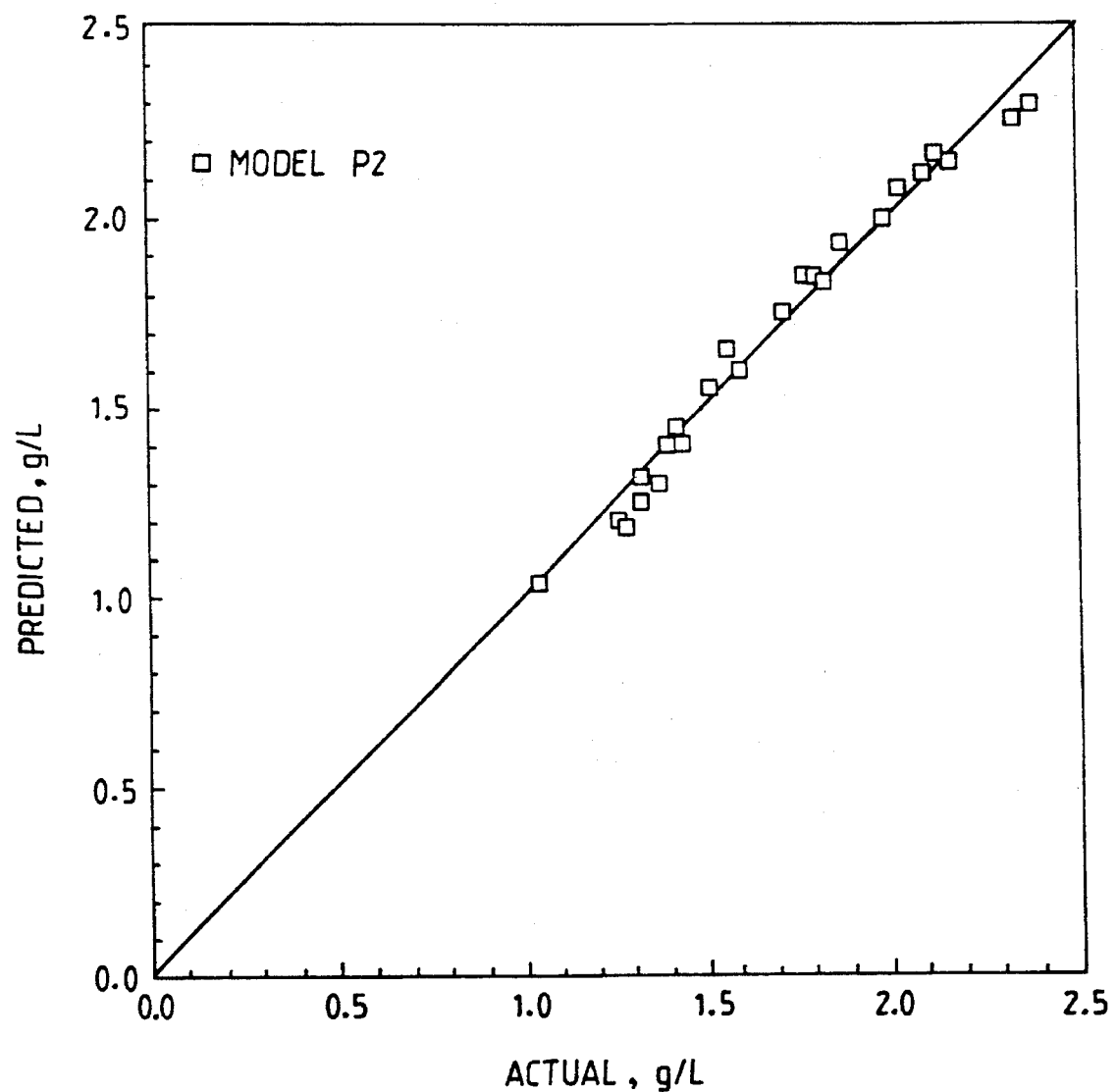
Figure 17:
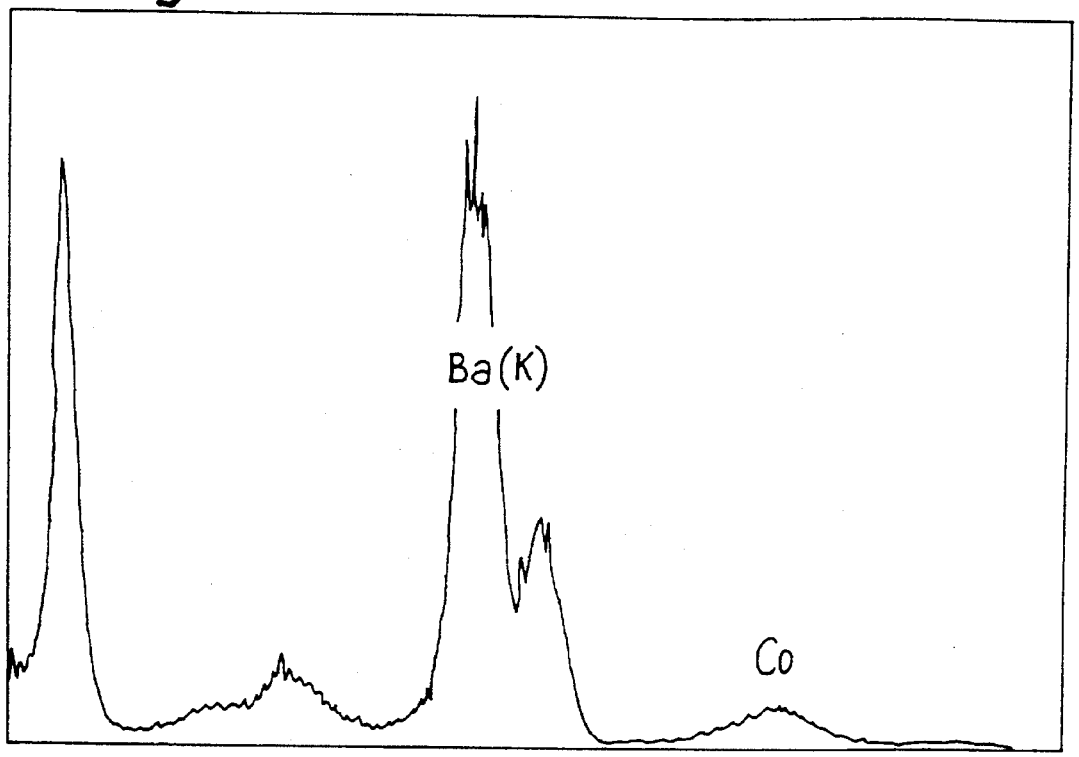
FIGS. 17 and 18 show XRF spectra of a drilling mud obtained using Am 241 and Fe 55 sources respectively, energy increases from left to fight, count rate is plotted vertically.
Figure 18:
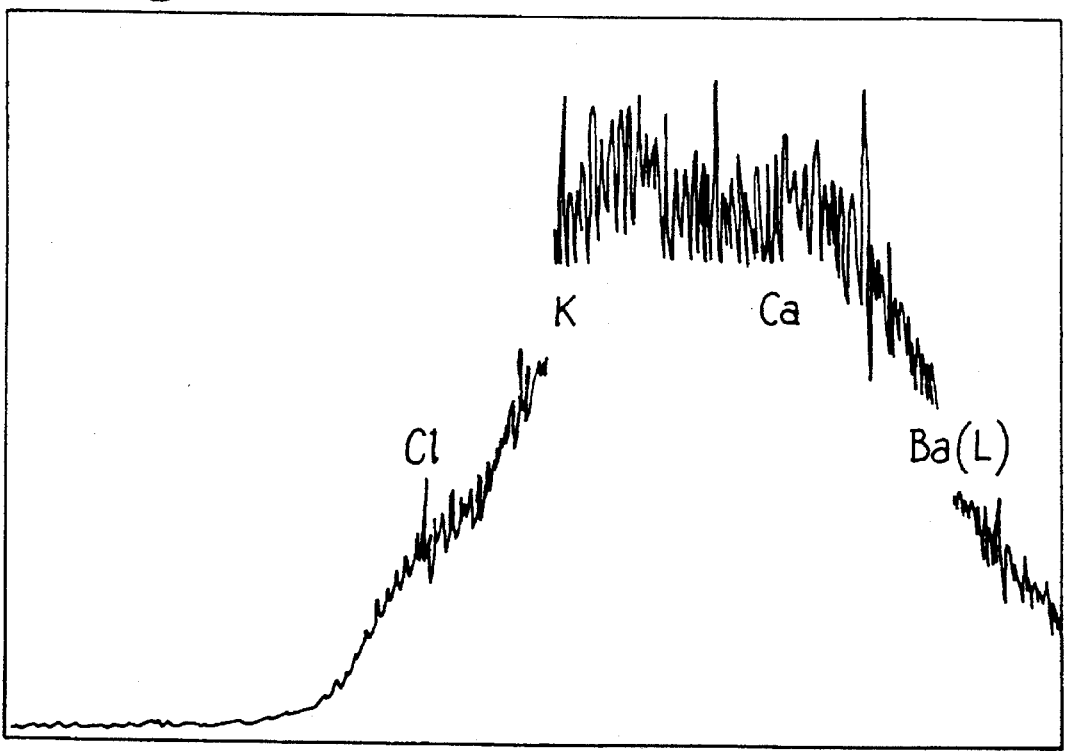

In the following examples, the system described below was used both as a laboratory test environment and as a system which could be applied to a rig environment. The system uses the Lab-X 1000 (Oxford Analytical Instruments), a portable (20 kg) energy dispersive spectrometer, fitted for our purposes with an Am 241 gamma-ray source and sealed proportional counter, filled with $Xe/CH_4$ and an Fe 55 source with a sealed counter filled with $Ne/CH_4$. This combination provides the K-α and K-β fluorescence peaks from barium in addition to a well defined Compton scatter peak to account for matrix effects and K line fluorescence peaks for S, Cl, K, Ca, Cr and the Lα peak for $B_a$. The spectrum obtained from the Am 241 source is shown in FIG. 17 and as can be seen is dominated by the Ba (K) peak with a significant Compton scattering peak Co. The spectrum from the Fe 55 source shows several overlapping peaks including the Ba (L) peak which is found in part at the high energy end of the spectrum. Because the Ba peak for the Am 241 source does not involve significant interferences, a reasonable estimate can be obtained for Ba concentration from this spectrum using a PLS algorithm. This estimate can then be used in the PLS algorithm applied to the Fe 55 spectrum since it will provide a good estimation of the contribution of the Ba (L) peak to the spectrum and so allow better estimation of the other unknowns. Once the Fe 55 spectrum is analysed, an estimation of Z and possibly SG can be obtained which can in turn be applied to a new PLS algorithm to analyse the Am 241 spectrum a second time.

The technique necessary for using XRF for analysis of drilling mud includes the following steps.

(1) A large number of data points selected from the spectral information is obtained. The Lab-X 1000 uses a 256 channel multichannel analyser. Windows containing the Ba K lines and the Compton peak from the Am 241 spectrum are isolated and their ratios determined. All data points from the Fe 55 spectrum are used, starting with the S fluorescence. Some ratioing of spectral information is done.

(2) The calcium concentration in the mud filtrate is determined in the conventional manner by EDTA titration. For oil based muds the oil / water volume ratio is determined. In the case of calibration samples, this information is known from the make-up of the sample. All of this information, together with the mud density, is input into the PLS algorithm, with the spectral information prepared as per the previous step.

(3) In the calibration stage steps (1) and (2) are repeated for each of the calibration samples, and the composition of each of the samples is input into the PLS algorithm. Suitable compositional categories are: barite, LGS not containing Ca., LGS containing Ca, soluble K, Cl, water content, oil content The PLS algorithm is then run to produce a calibration model.

(4) In the prediction phase unknowns are run by the XRF analyser and density, oil/water ratio and soluble calcium are input into the calibration model. The following compositional information is then produced: barite, LGS not containing Ca, LGS containing Ca, soluble K, Cl, water content, oil content.

Table 1 below shows the compositions of a series of calibration samples which were used to construct a calibration model using the PLS algorithm. Table 2 shows the compositions of the samples used to validate the calibration model. The results of the calibration step for Ba,Ca,K,Cl, LGS, $H_2O$,Z and SG are shown in Tables 3–10 and FIGS. 1–8. Tables 11–18 and FIGS. 9–16 show the results of the prediction of Ba,Ca,K,Cl, LGS, $H_2O$,Z and SG for the samples in the validation set using the calibration model. In the various examples, predictions have been made with the various models summarised below. These can be divided into two main groups, those which have SG (mud density) input into the model and those which have no input of SG. Obviously, the prediction of SG can only use a model which does not have SG as an input.

DESCRIPTION OF CALIBRATION MODELS USED IN THE EXAMPLE

Input elements

H1=a set of individual channels in the Fe 55 spectrum comprising the Cl, K, Ca, and Ba(L) peak areas.

H2=a set of individual channels in the Am 241 spectrum comprising the BA(K) and Co peak areas Ba/Co=the summation of the channels containing the Ba(K) peak area divided by the summation of the channels containing the Co peak area. The first, second and third powers of this ratio are input.

Z=the average atomic weight of the sample. Calculated for the calibration samples from weight fractions and molecular formulae of components making up the sample or predicted by Model P1 in the case of validation samples and unknowns. The first, second and third powers of Z are input.

SG=the density of the sample. Calculated for the calibration samples from weight fractions and densities of components making up the sample. In the case of validation samples and unknowns SG as an input is predicted by Model P1 or is obtained by direct measurement. The first, second and third powers of SG are input Composition of models in terms of input elements In the table X indicates that a particular input element is present.

| Model name | H1 | H2 | Ba/Co | Z | SG |
|---|---|---|---|---|---|
| P1 |  | X | X |  |  |
| PA |  |  | X | X | X |
| P2 | X |  | X |  |  |
| PR01 | X |  | X | X | X |
| PE |  |  | X |  | X |
| PG | X |  |  | X |  |

Outputs

In the Table X indicates that a particular output is predicted by the models listed; X* indicates the preferred way of prediction of an output.

| Model name | Ba | Cl | K | Ca | LGS | H2O | Z | SG |
|---|---|---|---|---|---|---|---|---|
| P1 | X |  |  |  | X | X | X* | X |
| PA | X* |  |  |  | X | X |  |  |
| P2 | X | X* | X | X | X* | X* | X | X* |
| PR01 | X | X | X* | X* | X | X |  |  |
| PE | X* |  |  |  | X | X | X* |  |
| PG | X | X* | X* | X* | X* | X* | X |  |

Combinations of calibration models

If density is used as an input then the two models PE and PG will serve to provide all outputs.

If density is not used as an input then a two stage process is followed. In the first stage Models P1 and P2 provide predicted values for Z and SG. Barite is produced in the second stage by Model PA, which uses the predicted Z and SG as inputs. Similarly K and Ca are produced by Model PR01. Values for Cl, LGS and H2O are taken directly from the prediction by Model P2 in the first stage.

| | SUMMARY OF CORRELATION COEFFICIENTS | | | | | |
|---|---|---|---|---|---|---|
| | Models Predicting Density | | | Models using Density as Input | | |
| Component (Property) | Model no. | Calibration corr. coeff. | Validation corr. coeff. | Model no. | Calibration corr. coeff. | Validation corr. coeff. |
| Barite | PA | 0.999 | 0.998 | PE | 0.999 | 0.999 |
| Chloride | P2 | 0.917 | 0.954 | PG | 0.892 | 0.947 |
| Potassium | PR01 | 0.953 | 0.952 | PG | 0.894 | 0.943 |
| Calcium | PR01 | 0.946 | 0.873 | PG | 0.911 | 0.895 |
| Water | P2 | 0.979 | 0.958 | PG | 0.981 | 0.991 |
| LGS | P2 | 0.974 | 0.937 | PG | 0.985 | 0.980 |

-continued

| | SUMMARY OF CORRELATION COEFFICIENTS | | | | | |
|---|---|---|---|---|---|---|
| | Models Predicting Density | | | Models using Density as Input | | |
| Component (Property) | Model no. | Calibration corr. coeff. | Validation corr. coeff. | Model no. | Calibration corr. coeff. | Validation corr. coeff. |
| Z | P1 | 0.999 | 0.998 | PE | 0.996 | 0.998 |
| SG | P2 | 0.989 | 0.981 | | | |

TABLE 1

CONCENTRATIONS (g/l): Calibration set

| SAMPLE | BaSO$_4$ | CaCO$_3$ | KNO$_3$ | KCL | NaCL | H$_2$O | POLYMER |
|---|---|---|---|---|---|---|---|
| 1 | 3.19 | 3.47 | 37.12 | 0.00 | 75.16 | 954.43 | 7.5 |
| 2 | 5.79 | 1.52 | 6.71 | 0.00 | 16.29 | 979.71 | 7.5 |
| 4 | 10.34 | 0.60 | 2.39 | 0.00 | 31.13 | 986.87 | 7.5 |
| 5 | 16.48 | 167.60 | 3.11 | 0.00 | 9.90 | 926.38 | 7.5 |
| 7 | 27.54 | 63.11 | 0.00 | 160.46 | 5.99 | 897.65 | 7.5 |
| 8 | 31.57 | 250.58 | 8.34 | 0.00 | 107.97 | 852.49 | 7.5 |
| 10 | 44.07 | 93.38 | 0.00 | 91.32 | 91.88 | 885.14 | 7.5 |
| 11 | 55.20 | 280.64 | 0.60 | 0.00 | 17.36 | 874.56 | 7.5 |
| 13 | 76.76 | 178.26 | 10.30 | 0.00 | 87.58 | 882.31 | 7.5 |
| 14 | 83.62 | 81.62 | 26.94 | 0.00 | 48.22 | 915.91 | 7.5 |
| 16 | 101.62 | 140.70 | 0.00 | 190.71 | 11.89 | 841.29 | 7.5 |
| 17 | 107.61 | 22.95 | 1.92 | 0.00 | 15.01 | 959.50 | 7.5 |
| 19 | 126.05 | 198.45 | 95.71 | 0.00 | 144.61 | 796.48 | 7.5 |
| 20 | 136.11 | 130.28 | 5.11 | 0.00 | 28.46 | 897.72 | 7.5 |
| 22 | 162.65 | 221.24 | 51.81 | 0.00 | 220.44 | 774.88 | 7.5 |
| 23 | 170.00 | 147.09 | 72.05 | 0.00 | 89.21 | 842.61 | 7.5 |
| 26 | 211.15 | 227.11 | 8.90 | 0.00 | 44.23 | 841.96 | 7.5 |
| 28 | 247.59 | 155.43 | 0.00 | 41.71 | 203.76 | 794.38 | 7.5 |
| 29 | 258.04 | 115.55 | 0.00 | 173.62 | 78.03 | 746.03 | 7.5 |
| 31 | 290.69 | 15.37 | 7.18 | 0.00 | 11.38 | 911.35 | 7.5 |
| 32 | 308.73 | 89.73 | 68.93 | 0.00 | 71.65 | 832.68 | 7.5 |
| 34 | 347.21 | 106.53 | 1.72 | 0.00 | 248.27 | 789.62 | 7.5 |
| 35 | 352.97 | 77.95 | 104.90 | 0.00 | 109.97 | 799.86 | 7.5 |
| 37 | 386.38 | 283.72 | 4.71 | 0.00 | 79.63 | 772.99 | 7.5 |
| 38 | 399.65 | 184.80 | 0.92 | 0.00 | 149.60 | 741.59 | 7.5 |
| 40 | 432.98 | 58.47 | 35.48 | 0.00 | 36.32 | 851.16 | 7.5 |
| 41 | 448.96 | 36.84 | 0.00 | 114.28 | 130.64 | 787.44 | 7.5 |
| 43 | 486.32 | 203.88 | 113.28 | 0.00 | 123.54 | 714.11 | 7.5 |
| 44 | 510.11 | 172.15 | 129.32 | 0.00 | 137.71 | 707.61 | 7.5 |
| 46 | 545.59 | 67.26 | 89.73 | 0.00 | 96.99 | 776.42 | 7.5 |
| 47 | 551.93 | 208.95 | 0.00 | 182.85 | 22.35 | 707.88 | 7.5 |
| 49 | 571.69 | 229.74 | 6.19 | 0.00 | 10.90 | 772.33 | 7.5 |
| 50 | 591.24 | 49.09 | 0.32 | 0.00 | 19.36 | 830.92 | 7.5 |
| 52 | 633.84 | 112.80 | 54.80 | 0.00 | 62.07 | 768.51 | 7.5 |
| 53 | 650.74 | 138.90 | 0.00 | 68.17 | 155.59 | 707.85 | 7.5 |
| 55 | 697.11 | 276.85 | 0.00 | 142.10 | 53.29 | 651.52 | 7.5 |
| 56 | 722.76 | 267.54 | 44.70 | 0.00 | 84.14 | 684.56 | 7.5 |
| 58 | 758.48 | 33.37 | 49.41 | 0.00 | 171.87 | 727.95 | 7.5 |
| 59 | 778.25 | 259.40 | 119.66 | 0.00 | 147.24 | 623.27 | 7.5 |
| 61 | 823.79 | 135.11 | 18.56 | 0.00 | 228.07 | 664.30 | 7.5 |
| 62 | 843.51 | 25.07 | 137.86 | 0.00 | 103.58 | 645.81 | 7.5 |
| 64 | 888.54 | 238.65 | 42.51 | 0.00 | 92.00 | 659.27 | 7.5 |
| 65 | 908.86 | 44.51 | 2.00 | 0.00 | 222.65 | 684.30 | 7.5 |
| 68 | 981.42 | 117.95 | 60.39 | 0.00 | 77.23 | 672.20 | 7.5 |
| 70 | 1027.54 | 13.49 | 0.00 | 134.43 | 93.76 | 669.19 | 7.5 |
| 71 | 1048.68 | 293.69 | 121.66 | 0.00 | 99.39 | 559.80 | 7.5 |
| 73 | 1099.62 | 102.02 | 2.79 | 0.00 | 12.25 | 700.57 | 7.5 |
| 74 | 1129.96 | 72.76 | 66.26 | 0.00 | 156.06 | 611.56 | 7.5 |
| 75 | 1176.57 | 272.97 | 74.04 | 0.00 | 177.34 | 532.17 | 7.5 |
| 77 | 1206.01 | 18.16 | 20.56 | 0.00 | 168.64 | 646.01 | 7.5 |
| 79 | 1256.44 | 192.31 | 39.24 | 0.00 | 195.78 | 548.07 | 7.5 |
| 80 | 1276.45 | 59.99 | 3.31 | 0.00 | 8.70 | 676.66 | 7.5 |
| 82 | 1320.36 | 287.02 | 7.38 | 0.00 | 12.89 | 584.06 | 7.5 |
| 83 | 1356.87 | 56.20 | 0.00 | 61.19 | 155.86 | 583.58 | 7.5 |
| 85 | 1412.27 | 163.45 | 0.00 | 197.77 | 30.45 | 472.58 | 7.5 |
| 88 | 1531.75 | 217.05 | 9.58 | 0.00 | 174.43 | 474.06 | 7.5 |
| 89 | 1566.38 | 104.50 | 0.00 | 122.88 | 45.50 | 538.00 | 7.5 |

TABLE 2

CONCENTRATIONS (g/l): Validation set

| SAMPLE | BaSO$_4$ | CaCO$_3$ | KNO$_3$ | KCL | NACL | H$_2$O | POLYMER |
|---|---|---|---|---|---|---|---|
| 9 | 38.32 | 17.28 | 3.91 | 0.00 | 4.11 | 974.34 | 7.5 |
| 12 | 67.30 | 123.33 | 64.28 | 0.00 | 193.18 | 837.04 | 7.5 |
| 18 | 119.46 | 235.41 | 46.70 | 0.00 | 179.53 | 787.59 | 7.5 |
| 21 | 154.39 | 109.09 | 13.69 | 0.00 | 237.4 | 816.96 | 7.5 |
| 24 | 183.72 | 7.90 | 86.13 | 0.00 | 121.86 | 869.09 | 7.5 |
| 27 | 226.63 | 248.19 | 0.00 | 148.40 | 36.12 | 776.21 | 7.5 |
| 30 | 273.21 | 20.48 | 22.67 | 0.00 | 128.92 | 875.48 | 7.5 |
| 33 | 323.82 | 214.06 | 0.00 | 58.27 | 170.03 | 748.71 | 7.5 |
| 36 | 363.80 | 42.43 | 7.86 | 0.00 | 131.72 | 846.63 | 7.5 |
| 39 | 424.81 | 7.58 | 58.47 | 0.00 | 100.50 | 835.05 | 7.5 |
| 42 | 466.99 | 98.31 | 3.59 | 0.00 | 7.30 | 850.61 | 7.5 |
| 48 | 559.20 | 29.54 | 144.69 | 0.00 | 115.55 | 752.55 | 7.5 |
| 51 | 615.48 | 126.65 | 2.59 | 0.00 | 5.19 | 809.19 | 7.5 |
| 54 | 678.47 | 242.80 | 28.34 | 0.00 | 233.70 | 651.85 | 7.5 |
| 57 | 740.92 | 187.29 | 10.70 | 0.00 | 182.81 | 690.71 | 7.5 |
| 60 | 797.00 | 159.58 | 11.38 | 0.00 | 13.57 | 743.39 | 7.5 |
| 63 | 867.67 | 254.06 | 0.00 | 177.42 | 85.14 | 595.21 | 7.5 |
| 66 | 930.02 | 85.21 | 4.19 | 0.00 | 25.74 | 738.27 | 7.5 |
| 69 | 1000.86 | 76.16 | 5.91 | 0.00 | 82.22 | 709.60 | 7.5 |
| 72 | 1076.88 | 206.08 | 0.00 | 167.76 | 52.61 | 587.10 | 7.5 |
| 75 | 1152.46 | 176.14 | 0.00 | 72.98 | 131.44 | 584.71 | 7.5 |
| 78 | 1231.05 | 96.39 | 12.37 | 0.00 | 14.29 | 671.62 | 7.5 |
| 81 | 1297.94 | 8.30 | 25.27 | 0.00 | 24.08 | 590.14 | 7.5 |
| 84 | 1385.47 | 151.79 | 149.99 | 0.00 | 126.12 | 514.11 | 7.5 |
| 87 | 1495.00 | 128.33 | 102.30 | 0.00 | 140.42 | 510.87 | 7.5 |

TABLE 3

| BARITE | | mud density not used Model PA | | | mud density input Model PE | | |
|---|---|---|---|---|---|---|---|
| Sample | Actual | Pred. | Error, g/L | Error, % | Pred. | Error, g/L | Error, % |
| 1 | 3.2 | 5.7 | 2.5 | 79.8 | 9.0 | 5.8 | 180.6 |
| 2 | 5.8 | 2.5 | −3.3 | −57.2 | 5.7 | −0.1 | −1.0 |
| 4 | 10.3 | 7.0 | −3.4 | −32.7 | 10.6 | 0.3 | 2.8 |
| 5 | 16.5 | 18.4 | 1.9 | 11.8 | 22.3 | 5.8 | 35.1 |
| 7 | 27.5 | 37.9 | 10.4 | 37.8 | 33.8 | 6.3 | 22.9 |
| 8 | 31.6 | 44.8 | 13.2 | 42.0 | 48.1 | 16.5 | 52.3 |
| 10 | 44.1 | 52.4 | 8.4 | 19.0 | 50.6 | 6.5 | 14.7 |
| 11 | 55.2 | 55.0 | −0.2 | −0.4 | 57.8 | 2.6 | 4.7 |
| 13 | 76.8 | 76.1 | −0.7 | −0.9 | 78.2 | 1.5 | 1.9 |
| 14 | 83.6 | 78.8 | −4.8 | −5.8 | 80.8 | −2.8 | −3.4 |
| 16 | 101.6 | 112.9 | 11.2 | 11.1 | 107.2 | 5.6 | 5.5 |
| 17 | 107.6 | 94.5 | −13.1 | −12.2 | 95.9 | −11.7 | −10.9 |
| 19 | 126.1 | 132.0 | 5.9 | 4.7 | 133.5 | 7.5 | 5.9 |
| 20 | 136.1 | 126.7 | −9.4 | −6.9 | 127.5 | −8.6 | −6.3 |
| 22 | 162.7 | 169.7 | 7.1 | 4.3 | 170.4 | 7.7 | 4.8 |
| 23 | 170.0 | 163.5 | −6.5 | −3.8 | 164.5 | −5.5 | −3.3 |
| 26 | 211.2 | 202.6 | −8.6 | −4.1 | 203.8 | −7.4 | −3.5 |
| 28 | 247.6 | 240.2 | −7.4 | −3.0 | 235.4 | −12.2 | −4.9 |
| 29 | 258.0 | 271.2 | 13.2 | 5.1 | 259.1 | 1.0 | 0.4 |
| 31 | 290.7 | 284.3 | −6.4 | −2.2 | 283.9 | −6.8 | −2.3 |
| 32 | 308.7 | 307.9 | −0.9 | −0.3 | 309.9 | 1.1 | 0.4 |
| 34 | 347.2 | 332.0 | −15.3 | −4.4 | 326.6 | −20.6 | −5.9 |
| 35 | 353.0 | 351.6 | −1.4 | −0.4 | 353.0 | 0.1 | 0.0 |
| 37 | 386.4 | 362.8 | −23.6 | −6.1 | 359.3 | −27.1 | −7.0 |
| 38 | 399.7 | 405.9 | 6.2 | 1.6 | 403.7 | 4.1 | 1.0 |
| 40 | 433.0 | 421.3 | −11.7 | −2.7 | 419.2 | −13.7 | −3.2 |
| 41 | 449.0 | 453.5 | 4.5 | 1.0 | 446.4 | −2.5 | −0.6 |
| 43 | 486.3 | 485.2 | −1.1 | −0.2 | 488.0 | 1.7 | 0.3 |
| 44 | 510.1 | 511.6 | 1.4 | 0.3 | 514.7 | 4.6 | 0.9 |
| 46 | 545.6 | 545.3 | −0.3 | −0.1 | 547.2 | 1.6 | 0.3 |
| 47 | 551.9 | 562.7 | 10.8 | 1.9 | 556.6 | 4.7 | 0.8 |
| 49 | 571.7 | 552.6 | −19.1 | −3.3 | 549.9 | −21.8 | −3.8 |
| 50 | 591.2 | 613.6 | 22.4 | 3.8 | 618.6 | 27.3 | 4.6 |
| 52 | 633.8 | 636.0 | 2.2 | 0.3 | 639.6 | 5.8 | 0.9 |
| 53 | 650.7 | 658.6 | 7.9 | 1.2 | 656.6 | 5.9 | 0.9 |
| 55 | 697.1 | 705.4 | 8.3 | 1.2 | 701.8 | 4.7 | 0.7 |
| 56 | 722.8 | 733.9 | 11.2 | 1.5 | 743.8 | 21.0 | 2.9 |
| 58 | 758.5 | 770.8 | 12.3 | 1.6 | 774.6 | 16.3 | 2.1 |
| 59 | 778.3 | 773.0 | −5.3 | −0.7 | 776.5 | −1.7 | −0.2 |

TABLE 3-continued

| | BARITE | mud density not used Model PA | | | mud density input Model PE | | |
|---|---|---|---|---|---|---|---|
| Sample | Actual | Pred. | Error, g/L | Error, % | Pred. | Error, g/L | Error, % |
| 61 | 823.6 | 814.9 | −8.8 | −1.1 | 812.1 | −11.7 | −1.4 |
| 62 | 843.5 | 839.6 | −3.9 | −0.5 | 828.8 | −14.7 | −1.7 |
| 64 | 888.5 | 888.7 | 0.2 | 0.0 | 895.7 | 7.1 | 0.8 |
| 65 | 908.9 | 902.2 | −6.6 | −0.7 | 897.2 | −11.6 | −1.3 |
| 68 | 981.4 | 987.4 | 5.9 | 0.6 | 993.4 | 12.0 | 1.2 |
| 70 | 1027.5 | 1032.7 | 5.2 | 0.5 | 1024.1 | −3.4 | −0.3 |
| 71 | 1048.7 | 1029.0 | −19.7 | −1.9 | 1028.4 | −20.3 | −1.9 |
| 73 | 1099.6 | 1117.4 | 17.8 | 1.6 | 1127.1 | 27.5 | 2.5 |
| 74 | 1130.0 | 1126.7 | −3.3 | −0.3 | 1126.2 | −3.8 | −0.3 |
| 76 | 1176.6 | 1195.4 | 18.8 | 1.6 | 1207.6 | 31.0 | 2.6 |
| 77 | 1206.0 | 1206.0 | 0.0 | 0.0 | 1208.2 | 2.2 | 0.2 |
| 79 | 1256.4 | 1273.7 | 17.3 | 1.4 | 1285.2 | 28.8 | 2.3 |
| 80 | 1276.5 | 1258.2 | −18.3 | −1.4 | 1252.8 | −23.7 | −1.9 |
| 82 | 1320.4 | 1317.4 | −3.0 | −0.2 | 1327.7 | 7.3. | 0.6 |
| 83 | 1358.9 | 1331.0 | −25.9 | −1.9 | 1318.2 | −38.7 | −2.8 |
| 85 | 1412.3 | 1428.8 | 16.5 | 1.2 | 1417.3 | 5.0 | 0.4 |
| 88 | 1531.8 | 1532.2 | 0.5 | 0.0 | 1533.0 | 1.3 | 0.1 |
| 89 | 1566.4 | 1554.9 | −11.5 | −0.7 | 1549.1 | −17.3 | −1.1 |

TABLE 4

| | CALCIUM | mud density not used Model PR01 | | | mud density input Model PG | | |
|---|---|---|---|---|---|---|---|
| Sample | Actual | Pred. | Error, g/L | Error, % | Pred. | Error, g/L | Error, % |
| 4 | 0.2 | −4.7 | −4.9 | −2060.0 | −6.0 | −6.2 | −2579.3 |
| 2 | 0.6 | −4.5 | −5.1 | −832.2 | −3.5 | −4.1 | −675.3 |
| 1 | 1.4 | 1.1 | −0.3 | −21.3 | −2.4 | −3.7 | −269.4 |
| 70 | 5.4 | 13.5 | 8.1 | 149.7 | 25.2 | 19.8 | 366.9 |
| 31 | 6.1 | −1.6 | −7.8 | −126.7 | 0.2 | −5.9 | −96.1 |
| 77 | 7.3 | 13.4 | 6.1 | 84.3 | 16.2 | 8.9 | 122.5 |
| 17 | 9.2 | 4.5 | −4.7 | −50.7 | 5.1 | −4.1 | −44.6 |
| 62 | 10.0 | 23.2 | 13.2 | 131.3 | 22.2 | 12.2 | 121.4 |
| 58 | 13.3 | 19.1 | 5.8 | 43.4 | 24.1 | 10.8 | 80.9 |
| 41 | 14.7 | 18.6 | 3.9 | 26.4 | 29.7 | 15.0 | 101.8 |
| 65 | 17.8 | 26.1 | 8.3 | 46.6 | 28.1 | 10.3 | 58.0 |
| 50 | 19.6 | 9.1 | −10.5 | −53.6 | 11.9 | −7.7 | −39.2 |
| 83 | 22.5 | 31.0 | 8.5 | 37.8 | 44.2 | 21.7 | 96.6 |
| 40 | 23.4 | 25.6 | 2.2 | 9.3 | 26.7 | 3.3 | 14.3 |
| 80 | 24.0 | 18.1 | −5.2 | −24.5 | 8.2 | −15.8 | −65.9 |
| 7 | 25.2 | 30.6 | 5.4 | 21.2 | 24.2 | −1.1 | −4.2 |
| 46 | 26.9 | 35.5 | 8.6 | 32.0 | 36.9 | 10.0 | 37.1 |
| 74 | 29.1 | 39.0 | 9.9 | 34.0 | 37.4 | 8.3 | 28.5 |
| 35 | 31.2 | 43.4 | 12.2 | 39.2 | 39.6 | 8.4 | 27.0 |
| 14 | 32.6 | 36.0 | 3.4 | 10.3 | 36.5 | 3.9 | 11.9 |
| 32 | 35.9 | 39.4 | 3.5 | 9.7 | 39.6 | 3.7 | 10.2 |
| 10 | 37.3 | 28.9 | −8.5 | −22.6 | 30.1 | −7.2 | −19.4 |
| 73 | 40.8 | 29.4 | −11.4 | −28.1 | 19.3 | −21.5 | −52.7 |
| 89 | 41.8 | 52.3 | 10.5 | 25.1 | 51.4 | 9.6 | 22.8 |
| 34 | 42.6 | 39.1 | −3.5 | −8.2 | 40.2 | −2.4 | −5.6 |
| 52 | 45.1 | 47.5 | 2.4 | 5.3 | 47.3 | 2.2 | 4.8 |
| 29 | 46.2 | 37.9 | −8.3 | −17.9 | 39.8 | −6.4 | −13.8 |
| 68 | 47.2 | 50.7 | 3.6 | 7.5 | 43.8 | −3.4 | −7.2 |
| 20 | 52.1 | 59.3 | 7.2 | 13.9 | 60.9 | 8.8 | 16.9 |
| 61 | 54.0 | 51.5 | −2.6 | −4.8 | 61.2 | 7.2 | 13.3 |
| 53 | 55.6 | 59.1 | 3.6 | 6.4 | 58.0 | 2.4 | 4.4 |
| 16 | 56.3 | 54.1 | −2.2 | −3.9 | 48.1 | −8.1 | −14.4 |
| 23 | 58.6 | 64.5 | 5.6 | 9.6 | 59.5 | 0.6 | 1.1 |
| 28 | 62.2 | 59.5 | −2.7 | −4.4 | 52.7 | −9.5 | −15.3 |
| 85 | 65.4 | 48.6 | −16.7 | −25.6 | 63.4 | −1.9 | −3.0 |
| 5 | 67.0 | 92.2 | 25.2 | 37.6 | 95.4 | 28.3 | 42.3 |
| 44 | 68.9 | 75.5 | 6.6 | 9.7 | 73.1 | 4.2 | 6.1 |
| 13 | 71.3 | 77.6 | 6.5 | 9.1 | 76.2 | 4.9 | 6.2 |
| 38 | 73.9 | 61.6 | −12.4 | −16.7 | 63.0 | −10.9 | −14.7 |
| 79 | 76.9 | 75.3 | −1.7 | −2.2 | 78.8 | 1.7 | 2.2 |
| 19 | 79.4 | 76.4 | −3.0 | −3.8 | 72.1 | −7.3 | −9.2 |
| 43 | 81.6 | 87.2 | 5.7 | 6.9 | 80.4 | −1.1 | −1.4 |
| 47 | 83.6 | 69.2 | −14.4 | −17.3 | 86.0 | 2.4 | 2.9 |
| 88 | 86.8 | 85.8 | −1.0 | −1.1 | 85.6 | −1.2 | −1.4 |

TABLE 4-continued

| CALCIUM | | mud density not used | | | mud density input | | |
|---|---|---|---|---|---|---|---|
| | | Model PR01 | | | Model PG | | |
| Sample | Actual | Pred. | Error, g/L | Error, % | Pred. | Error, g/L | Error, % |
| 22 | 88.5 | 77.5 | −11.0 | −12.4 | 72.1 | −16.4 | −18.5 |
| 26 | 90.8 | 90.3 | −0.5 | −0.6 | 93.1 | 2.2 | 2.4 |
| 49 | 91.9 | 85.5 | −6.4 | −6.9 | 87.4 | −4.5 | −4.9 |
| 64 | 95.5 | 91.6 | −3.8 | −4.0 | 85.7 | −9.8 | −10.3 |
| 8 | 100.2 | 89.6 | −10.4 | −10.4 | 94.7 | −5.6 | −5.6 |
| 59 | 103.8 | 107.2 | 3.4 | 3.3 | 103.4 | −0.4 | −0.4 |
| 56 | 107.0 | 106.3 | −0.7 | −0.7 | 93.9 | −13.1 | −12.3 |
| 76 | 109.2 | 113.2 | 4.7 | 4.3 | 108.1 | −1.1 | −1.0 |
| 55 | 110.7 | 97.1 | −13.6 | −12.3 | 96.2 | −14.6 | −13.2 |
| 11 | 112.3 | 119.8 | 7.6 | 6.8 | 135.1 | 22.8 | 20.3 |
| 37 | 113.5 | 109.7 | −3.8 | −3.4 | 104.9 | −8.6 | −7.6 |
| 82 | 114.0 | 99.3 | −15.5 | −13.5 | 88.7 | −26.1 | −22.8 |
| 71 | 117.5 | 122.6 | 5.1 | 4.4 | 117.1 | −0.4 | −0.3 |

TABLE 5

| POTASSIUM | | mud density not used | | | mud density input | | |
|---|---|---|---|---|---|---|---|
| | | Model PR01 | | | Model PG | | |
| Sample | Actual | Pred. | Error, g/L | Error, % | Pred. | Error, g/L | Error, % |
| 50 | 0.1 | −0.4 | −0.5 | −442.4 | −0.4 | −0.5 | −385.5 |
| 11 | 0.2 | 5.5 | 5.2 | 2254.4 | 0.1 | −0.1 | −51.5 |
| 38 | 0.4 | 8.5 | 8.1 | 2287.2 | −1.8 | −2.2 | −607.0 |
| 34 | 0.7 | −2.5 | −3.2 | −475.0 | −1.0 | −1.6 | −243.5 |
| 17 | 0.7 | −6.8 | −7.5 | −1008.8 | −4.9 | −5.7 | −765.2 |
| 65 | 0.8 | 7.0 | 6.2 | 804.4 | 6.0 | 5.3 | 678.7 |
| 4 | 0.9 | −1.8 | −2.7 | −291.9 | −2.7 | −3.7 | −395.3 |
| 73 | 1.1 | −4.4 | −5.5 | −506.2 | 6.4 | 5.4 | 495.6 |
| 5 | 1.2 | −2.0 | −3.2 | −265.8 | −7.2 | −8.4 | −694.8 |
| 80 | 1.3 | 7.5 | 6.2 | 482.7 | 7.4 | 6.1 | 475.0 |
| 37 | 1.8 | 0.5 | −1.3 | −73.5 | 3.5 | 1.7 | 94.0 |
| 20 | 2.0 | −0.3 | −2.2 | −113.3 | −4.6 | −6.6 | −332.5 |
| 49 | 2.4 | 11.3 | 8.9 | 370.6 | 7.2 | 4.8 | 201.1 |
| 2 | 2.6 | 6.2 | 3.6 | 138.6 | 0.9 | −1.7 | −65.3 |
| 31 | 2.8 | −5.8 | −8.6 | −308.5 | 1.4 | −1.4 | −48.6 |
| 82 | 2.9 | 6.6 | 3.7 | 130.8 | 19.5 | 16.6 | 581.6 |
| 8 | 3.2 | −1.7 | −4.9 | −152.1 | −2.8 | −6.1 | −188.0 |
| 26 | 3.4 | 5.1 | 1.7 | 48.3 | 3.0 | −0.5 | −14.0 |
| 88 | 3.7 | 17.3 | 13.6 | 367.7 | 21.3 | 17.6 | 473.5 |
| 13 | 4.0 | −0.5 | −4.5 | −113.7 | −2.3 | −6.3 | −158.2 |
| 61 | 7.2 | 16.5 | 9.3 | 130.1 | 11.7 | 4.5 | 62.5 |
| 77 | 8.0 | 13.3 | 5.4 | 67.8 | 13.4 | 5.4 | 68.3 |
| 14 | 10.4 | 15.5 | 5.1 | 48.7 | 10.5 | 0.1 | 0.5 |
| 40 | 13.7 | 16.0 | 2.3 | 16.8 | 16.8 | 3.1 | 22.4 |
| 1 | 14.4 | 17.7 | 3.4 | 23.4 | 22.7 | 8.3 | 57.9 |
| 79 | 15.2 | 20.1 | 4.9 | 32.3 | 24.4 | 9.2 | 60.5 |
| 64 | 16.5 | 16.3 | −0.1 | −0.9 | 23.8 | 7.3 | 44.6 |
| 56 | 17.3 | 13.0 | −4.3 | −25.1 | 24.0 | 6.7 | 38.9 |
| 58 | 19.1 | 16.0 | −3.2 | −16.5 | 20.9 | 1.7 | 9.1 |
| 22 | 20.1 | 13.0 | −7.1 | −35.4 | 14.9 | −5.2 | −25.7 |
| 52 | 21.2 | 21.1 | −0.1 | −0.7 | 24.2 | 3.0 | 14.1 |
| 28 | 21.9 | 14.9 | −7.0 | −31.8 | 17.1 | −4.8 | −21.7 |
| 68 | 23.4 | 19.6 | −3.8 | −16.2 | 26.3 | 2.9 | 12.5 |
| 74 | 25.6 | 23.4 | −2.2 | −8.6 | 26.4 | 0.8 | 3.1 |
| 32 | 26.7 | 32.3 | 5.7 | 21.3 | 30.5 | 3.8 | 14.4 |
| 23 | 27.9 | 30.2 | 2.4 | 8.5 | 33.1 | 5.2 | 18.8 |
| 76 | 28.7 | 24.4 | −4.2 | −14.8 | 35.7 | 7.0 | 24.5 |
| 83 | 32.1 | 45.4 | 13.4 | 41.7 | 30.3 | −1.8 | −5.5 |
| 46 | 34.7 | 33.6 | −1.1 | −3.1 | 37.1 | 2.4 | 6.9 |
| 53 | 35.7 | 39.6 | 3.9 | 10.9 | 30.6 | −5.1 | −14.4 |
| 19 | 37.0 | 33.2 | −3.9 | −10.5 | 36.9 | −0.2 | −0.4 |
| 35 | 40.6 | 42.8 | 2.2 | 5.4 | 44.3 | 3.7 | 9.1 |
| 43 | 43.8 | 38.8 | −5.0 | −11.4 | 44.2 | 0.3 | 0.8 |
| 59 | 46.3 | 41.2 | −5.1 | −11.0 | 45.9 | −0.4 | −1.0 |
| 71 | 47.1 | 48.4 | 1.3 | 2.8 | 52.2 | 5.1 | 10.9 |
| 10 | 47.9 | 47.9 | 0.1 | 0.2 | 54.0 | 6.2 | 12.9 |
| 44 | 50.0 | 53.6 | 3.5 | 7.0 | 48.8 | −1.3 | −2.6 |
| 62 | 53.4 | 51.4 | −1.9 | −3.6 | 49.2 | −4.1 | −7.8 |
| 41 | 59.9 | 58.9 | −1.0 | −1.7 | 46.7 | −13.1 | −21.9 |

TABLE 5-continued

|  | | mud density not used | | | mud density input | | |
|---|---|---|---|---|---|---|---|
| POTASSIUM | | Model PR01 | | | Model PG | | |
| Sample | Actual | Pred. | Error, g/L | Error, % | Pred. | Error, g/L | Error, % |
| 89 | 64.4 | 57.8 | −6.5 | −10.2 | 52.3 | −12.1 | −18.8 |
| 70 | 70.4 | 58.6 | −11.9 | −16.8 | 50.2 | −20.2 | −28.7 |
| 55 | 74.5 | 70.4 | −4.1 | −5.5 | 67.0 | −7.5 | −10.1 |
| 7 | 84.1 | 98.1 | 14.0 | 16.6 | 110.9 | 26.8 | 31.9 |
| 29 | 91.0 | 91.2 | 0.2 | 0.3 | 83.3 | −7.7 | −8.4 |
| 47 | 95.8 | 96.8 | 2.9 | 3.1 | 81.1 | −14.7 | −15.4 |
| 16 | 99.9 | 101.7 | 1.6 | 1.8 | 111.7 | 11.9 | 11.8 |
| 85 | 103.6 | 81.7 | −21.9 | −21.2 | 63.9 | −39.8 | −38.4 |

TABLE 6

|  | | mud density not used | | | mud density input | | |
|---|---|---|---|---|---|---|---|
| CHLORIDE | | Model P2 | | | Model PG | | |
| Sample | Actual | Pred. | Error, g/L | Error, % | Pred. | Error, g/L | Error, % |
| 80 | 5.3 | 23.1 | 17.8 | 337.9 | 16.1 | 10.9 | 205.8 |
| 5 | 6.0 | −5.3 | −11.3 | −187.5 | −12.0 | −18.0 | −298.9 |
| 49 | 6.6 | 17.5 | 10.9 | 164.5 | 17.4 | 10.8 | 163.2 |
| 31 | 6.9 | −7.6 | −14.5 | −209.9 | 5.6 | −1.3 | −18.3 |
| 73 | 7.4 | 12.8 | 5.4 | 72.5 | 14.6 | 7.2 | 96.7 |
| 82 | 7.8 | 23.5 | 15.7 | 200.0 | 34.5 | 26.7 | 341.2 |
| 17 | 9.1 | −1.9 | −11.0 | −121.0 | 3.7 | −5.4 | −59.3 |
| 2 | 9.9 | 15.6 | 5.7 | 57.4 | 8.0 | −1.9 | −19.2 |
| 11 | 10.5 | −7.1 | −17.6 | −167.0 | −4.1 | −14.6 | −138.5 |
| 50 | 11.8 | 19.9 | 8.1 | 69.2 | 14.8 | 3.0 | 25.5 |
| 20 | 17.3 | 17.7 | 0.4 | 2.5 | 10.7 | −6.5 | −37.8 |
| 4 | 18.9 | 23.3 | 4.4 | 23.2 | 22.2 | 3.3 | 17.6 |
| 40 | 22.0 | 25.1 | 3.1 | 13.8 | 28.9 | 6.8 | 31.0 |
| 26 | 26.8 | 25.2 | −1.7 | −6.2 | 25.0 | −1.8 | −6.7 |
| 14 | 29.3 | 36.9 | 7.6 | 25.9 | 28.6 | −0.7 | −2.4 |
| 52 | 37.7 | 43.7 | 6.0 | 15.9 | 48.5 | 10.8 | 28.8 |
| 13 | 41.0 | 44.0 | 3.0 | 7.3 | 38.6 | −2.4 | −5.8 |
| 32 | 43.5 | 60.6 | 17.1 | 39.2 | 50.0 | 6.5 | 14.9 |
| 1 | 45.6 | 47.7 | 2.1 | 4.6 | 57.6 | 12.0 | 26.3 |
| 68 | 46.9 | 52.5 | 5.6 | 11.9 | 54.8 | 7.9 | 16.9 |
| 37 | 48.3 | 43.9 | −4.4 | −9.1 | 54.2 | 5.9 | 12.2 |
| 56 | 51.1 | 59.1 | 8.0 | 15.7 | 63.1 | 12.0 | 23.5 |
| 23 | 54.2 | 55.8 | 1.6 | 3.0 | 58.1 | 4.0 | 7.4 |
| 64 | 55.8 | 59.1 | 3.3 | 5.9 | 68.9 | 13.1 | 23.4 |
| 46 | 58.9 | 61.4 | 2.5 | 4.3 | 68.5 | 9.6 | 16.3 |
| 71 | 60.3 | 73.9 | 13.5 | 22.4 | 86.6 | 26.3 | 43.6 |
| 62 | 62.9 | 68.4 | 5.6 | 8.9 | 68.2 | 5.3 | 8.5 |
| 8 | 65.5 | 65.2 | −0.3 | −0.5 | 64.8 | −0.8 | −1.2 |
| 35 | 66.8 | 78.7 | 11.9 | 17.2 | 75.7 | 9.0 | 13.5 |
| 43 | 75.0 | 79.5 | 4.5 | 6.0 | 83.9 | 8.9 | 11.9 |
| 7 | 80.0 | 82.3 | 2.3 | 2.9 | 95.3 | 15.3 | 19.1 |
| 44 | 83.6 | 104.6 | 21.0 | 25.1 | 90.7 | 7.2 | 8.6 |
| 89 | 86.1 | 95.3 | 9.2 | 10.6 | 88.0 | 1.9 | 2.2 |
| 19 | 87.8 | 88.8 | 1.0 | 1.2 | 88.7 | 0.9 | 1.0 |
| 59 | 89.4 | 89.0 | −0.4 | −0.4 | 98.9 | 9.6 | 10.7 |
| 38 | 90.8 | 112.8 | 22.0 | 24.3 | 93.3 | 2.5 | 2.7 |
| 74 | 94.7 | 85.1 | −9.6 | −10.2 | 89.6 | −5.2 | −5.5 |
| 16 | 98.0 | 101.2 | 3.2 | 3.3 | 109.1 | 11.1 | 11.3 |
| 10 | 99.2 | 102.8 | 3.6 | 3.6 | 112.4 | 13.2 | 13.3 |
| 55 | 100.0 | 111.7 | 11.7 | 11.7 | 108.2 | 8.2 | 8.2 |
| 47 | 100.6 | 47.6 | −53.0 | −52.6 | 33.7 | −66.9 | −66.5 |
| 77 | 102.4 | 91.7 | −10.7 | −10.4 | 90.9 | −11.4 | −11.2 |
| 58 | 104.3 | 93.5 | −10.8 | −10.4 | 103.3 | −1.0 | −0.9 |
| 88 | 105.9 | 95.0 | −10.9 | −10.3 | 101.8 | −4.1 | −3.8 |
| 76 | 107.6 | 103.0 | −4.6 | −4.3 | 112.2 | 4.6 | 4.3 |
| 85 | 112.6 | 105.9 | −6.7 | −6.0 | 90.1 | −22.5 | −20.0 |
| 79 | 118.8 | 108.9 | −9.9 | −8.4 | 110.9 | −8.0 | −6.7 |
| 70 | 120.9 | 114.3 | −6.6 | −5.5 | 111.9 | −9.0 | −7.4 |
| 83 | 123.7 | 119.6 | −4.1 | −3.3 | 110.5 | −13.2 | −10.7 |
| 53 | 126.2 | 138.6 | 11.7 | 9.3 | 119.1 | −7.8 | −6.1 |
| 29 | 130.0 | 139.8 | 9.8 | 7.5 | 130.3 | 0.3 | 0.3 |
| 41 | 133.7 | 99.0 | −34.7 | −26.0 | 89.2 | −44.5 | −33.3 |
| 22 | 133.8 | 135.3 | 1.5 | 1.1 | 130.9 | −2.9 | −2.2 |
| 65 | 135.1 | 121.3 | −13.9 | −10.3 | 123.7 | −11.5 | −8.5 |

TABLE 6-continued

| CHLORIDE | | mud density not used Model P2 | | | mud density input Model PG | | |
|---|---|---|---|---|---|---|---|
| Sample | Actual | Pred. | Error, g/L | Error, % | Pred. | Error, g/L | Error, % |
| 61 | 138.4 | 123.0 | −15.4 | −11.2 | 126.7 | −11.7 | −8.5 |
| 28 | 143.5 | 143.7 | 0.1 | 0.1 | 142.4 | −1.1 | −0.8 |
| 34 | 150.7 | 139.0 | −11.7 | −7.7 | 147.2 | −3.5 | −2.3 |

TABLE 7

| LGS | | mud density not used Model P2 | | | mud density input Model PG | | |
|---|---|---|---|---|---|---|---|
| Sample | Actual | Pred. | Error, g/L | Error, % | Pred. | Error, g/L | Error, % |
| 2 | 21.31 | 31.14 | 9.83 | 46.10 | 22.77 | 1.46 | 6.85 |
| 4 | 25.83 | 41.98 | 16.14 | 62.48 | 31.44 | 5.60 | 21.68 |
| 7 | 59.03 | 81.78 | 22.75 | 38.53 | 63.47 | 4.44 | 7.52 |
| 1 | 63.23 | 44.29 | −18.95 | −29.96 | 34.19 | −29.04 | −45.93 |
| 17 | 72.63 | 31.31 | −41.32 | −56.89 | 93.81 | 21.18 | 29.15 |
| 10 | 117.74 | 132.49 | 14.73 | 12.51 | 117.26 | −0.50 | −0.42 |
| 5 | 120.50 | 191.09 | 70.51 | 58.48 | 141.68 | 21.10 | 17.50 |
| 14 | 126.35 | 100.12 | −26.23 | −20.76 | 121.64 | −4.71 | −3.73 |
| 16 | 138.37 | 161.25 | 22.88 | 16.54 | 154.15 | 15.78 | 11.40 |
| 31 | 145.24 | 112.22 | −33.02 | −22.73 | 174.77 | 29.53 | 20.33 |
| 20 | 155.96 | 175.75 | 19.79 | 12.69 | 175.21 | 19.25 | 12.34 |
| 13 | 178.87 | 207.46 | 28.59 | 15.98 | 182.39 | 3.52 | 1.97 |
| 11 | 205.68 | 207.31 | 1.63 | 0.79 | 226.76 | 21.08 | 10.25 |
| 29 | 213.68 | 219.70 | 6.02 | 2.82 | 224.15 | 10.47 | 4.90 |
| 8 | 218.33 | 217.39 | −0.94 | −0.43 | 206.98 | −11.35 | −5.20 |
| 23 | 244.94 | 177.08 | −67.86 | −27.70 | 213.48 | −31.46 | −12.84 |
| 26 | 253.43 | 228.05 | −25.38 | −10.01 | 267.74 | 14.31 | 5.65 |
| 40 | 256.81 | 258.79 | 1.98 | 0.77 | 270.94 | 14.13 | 5.50 |
| 32 | 258.82 | 257.71 | −1.11 | −0.43 | 249.17 | −9.65 | −3.73 |
| 41 | 265.77 | 290.50 | 24.73 | 9.31 | 311.92 | 46.15 | 17.36 |
| 28 | 282.75 | 317.50 | 34.75 | 12.29 | 290.77 | 8.02 | 2.84 |
| 50 | 288.08 | 349.69 | 61.61 | 21.39 | 306.25 | 18.17 | 6.31 |
| 19 | 293.95 | 230.19 | −63.76 | −21.69 | 236.92 | −57.03 | −19.40 |
| 35 | 307.11 | 258.11 | −49.00 | −15.96 | 278.13 | −28.98 | −9.44 |
| 34 | 313.00 | 337.89 | 24.89 | 7.95 | 325.36 | 12.36 | 3.95 |
| 22 | 325.59 | 296.61 | −28.98 | −8.90 | 289.92 | −35.67 | −10.96 |
| 38 | 342.20 | 376.25 | 34.05 | 9.95 | 342.46 | 0.26 | 0.08 |
| 46 | 365.56 | 331.69 | −33.87 | −9.27 | 352.75 | −12.81 | −3.50 |
| 47 | 368.73 | 414.84 | 46.11 | 12.51 | 403.53 | 34.80 | 9.44 |
| 37 | 370.84 | 370.63 | −0.21 | −0.06 | 383.34 | 12.50 | 3.37 |
| 49 | 388.62 | 421.14 | 32.52 | 8.37 | 406.91 | 18.29 | 4.71 |
| 52 | 394.03 | 386.06 | −7.97 | −2.02 | 393.50 | −0.53 | −0.13 |
| 53 | 419.82 | 465.09 | 45.27 | 10.78 | 456.05 | 36.23 | 8.63 |
| 58 | 437.60 | 455.34 | 17.74 | 4.05 | 436.90 | −0.70 | −0.16 |
| 43 | 447.97 | 395.26 | −52.71 | −11.77 | 410.79 | −37.18 | −8.30 |
| 44 | 454.15 | 402.81 | −51.34 | −11.30 | 412.92 | −41.23 | −9.08 |
| 70 | 475.38 | 522.57 | 47.19 | 9.93 | 529.73 | 54.35 | 11.43 |
| 55 | 481.36 | 522.43 | 41.07 | 8.53 | 516.94 | 35.58 | 7.39 |
| 62 | 494.99 | 494.39 | −0.60 | −0.12 | 422.66 | −72.33 | −14.61 |
| 65 | 497.06 | 548.40 | 51.34 | 10.33 | 511.79 | 14.73 | 2.96 |
| 56 | 525.89 | 567.63 | 41.74 | 7.94 | 517.72 | −8.17 | −1.55 |
| 73 | 527.77 | 566.28 | 38.51 | 7.30 | 496.06 | −31.71 | −6.01 |
| 61 | 528.68 | 501.39 | −27.27 | −5.16 | 548.75 | 20.09 | 3.80 |
| 68 | 549.56 | 558.26 | 8.70 | 1.58 | 521.52 | −28.04 | −5.10 |
| 80 | 574.27 | 559.99 | −14.28 | −2.49 | 543.44 | −30.83 | −5.37 |
| 64 | 578.54 | 559.91 | −18.63 | −3.22 | 572.56 | −5.98 | −1.03 |
| 77 | 593.69 | 587.01 | −6.68 | −1.13 | 583.59 | −10.10 | −1.70 |
| 59 | 614.65 | 544.73 | −69.92 | −11.38 | 586.03 | −28.62 | −4.66 |
| 74 | 618.22 | 615.54 | −2.68 | −0.43 | 587.28 | −30.94 | −5.00 |
| 83 | 660.96 | 643.20 | −17.76 | −2.69 | 702.05 | 41.09 | 6.22 |
| 85 | 698.73 | 743.44 | 44.71 | 6.40 | 720.25 | 21.52 | 3.08 |
| 71 | 728.90 | 670.93 | −57.97 | −7.95 | 701.69 | −27.21 | −3.73 |
| 82 | 732.61 | 737.75 | 5.14 | 0.70 | 715.27 | −17.34 | −2.37 |
| 89 | 732.73 | 719.08 | −13.65 | −1.86 | 765.17 | 32.44 | 4.43 |
| 79 | 741.00 | 717.82 | −23.18 | −3.13 | 741.63 | 0.63 | 0.09 |
| 76 | 770.58 | 747.66 | −22.92 | −2.97 | 772.15 | 1.57 | 0.20 |
| 88 | 842.56 | 805.83 | −36.73 | −4.36 | 848.06 | 5.50 | 0.65 |

TABLE 8

| | WATER | | mud density not used Model P2 | | | mud density input Model PG | | |
|---|---|---|---|---|---|---|---|---|
| Sample | Actual | Pred. | Error, g/L | Error, % | Pred. | Error, g/L | Error, % |
| 85 | 472.8 | 499.8 | 27.3 | 5.8 | 527.8 | 55.3 | 11.7 |
| 88 | 474.1 | 506.7 | 32.7 | 6.9 | 481.4 | 7.4 | 1.6 |
| 89 | 528.0 | 523.7 | -4.3 | -0.8 | 509.1 | -18.9 | -3.6 |
| 76 | 532.2 | 535.9 | 3.7 | 0.7 | 519.6 | -12.5 | -2.4 |
| 79 | 548.1 | 550.7 | 2.7 | 0.5 | 539.9 | -8.2 | -1.5 |
| 71 | 559.8 | 580.7 | 20.9 | 3.7 | 558.4 | -1.4 | -0.2 |
| 83 | 583.6 | 574.2 | -9.4 | -1.6 | 556.9 | -26.7 | -4.6 |
| 82 | 584.1 | 574.7 | -9.4 | -1.6 | 573.2 | -10.8 | -1.9 |
| 74 | 611.6 | 622.4 | 10.8 | 1.8 | 629.7 | 18.2 | 3.0 |
| 59 | 623.3 | 649.1 | 25.9 | 4.1 | 624.1 | 0.9 | 0.1 |
| 62 | 645.8 | 684.4 | 38.5 | 6.0 | 716.5 | 70.7 | 11.0 |
| 77 | 646.0 | 636.8 | -9.3 | -1.4 | 636.6 | -9.4 | -1.5 |
| 55 | 651.5 | 634.1 | -17.5 | -2.7 | 644.0 | -7.5 | -1.2 |
| 64 | 659.3 | 662.8 | 3.5 | 0.5 | 648.6 | -10.7 | -1.6 |
| 61 | 664.3 | 679.7 | 15.4 | 2.3 | 655.8 | -8.5 | -1.3 |
| 70 | 669.2 | 643.7 | -25.5 | -3.8 | 644.0 | -25.2 | -3.8 |
| 68 | 672.2 | 662.7 | -9.5 | -1.4 | 676.3 | 4.0 | 0.6 |
| 80 | 676.7 | 668.4 | -8.3 | -1.2 | 677.7 | 1.1 | 0.2 |
| 65 | 684.3 | 664.6 | -19.7 | -2.9 | 678.3 | -6.0 | -0.9 |
| 56 | 684.6 | 659.7 | -24.8 | -3.6 | 680.9 | -3.7 | -0.5 |
| 73 | 700.6 | 680.9 | -19.7 | -2.8 | 706.5 | 5.9 | 0.8 |
| 44 | 707.6 | 706.8 | -0.8 | -0.1 | 719.9 | 12.3 | 1.7 |
| 53 | 707.9 | 670.4 | -37.4 | -5.3 | 697.3 | -10.5 | -1.5 |
| 47 | 707.9 | 697.3 | -10.6 | -1.5 | 720.8 | 12.9 | 1.8 |
| 43 | 714.1 | 734.6 | 20.4 | 2.9 | 724.8 | 10.6 | 1.5 |
| 58 | 728.0 | 720.4 | -7.6 | -1.0 | 717.9 | -10.0 | -1.4 |
| 38 | 741.6 | 748.0 | 6.4 | 0.9 | 784.6 | 43.0 | 5.8 |
| 29 | 746.0 | 781.2 | 35.2 | 4.7 | 787.7 | 41.6 | 5.6 |
| 52 | 768.5 | 763.6 | -4.9 | -0.6 | 755.0 | -13.5 | -1.8 |
| 49 | 772.3 | 756.9 | -15.5 | -2.0 | 764.0 | -8.3 | -1.1 |
| 37 | 773.0 | 784.9 | 11.9 | 1.5 | 768.6 | -4.4 | -0.6 |
| 22 | 774.9 | 784.9 | 10.0 | 1.3 | 792.1 | 17.3 | 2.2 |
| 46 | 776.4 | 783.4 | 7.0 | 0.9 | 766.4 | -10.0 | -1.3 |
| 41 | 787.4 | 777.4 | -10.1 | -1.3 | 779.2 | -8.3 | -1.1 |
| 34 | 789.6 | 785.8 | -3.8 | -0.5 | 782.2 | -7.5 | -0.9 |
| 28 | 794.4 | 776.5 | -17.9 | -2.3 | 789.1 | -5.3 | -0.7 |
| 19 | 796.5 | 823.0 | 26.5 | 3.3 | 819.2 | 22.7 | 2.9 |
| 35 | 799.9 | 807.1 | 7.2 | 0.9 | 801.4 | 1.6 | 0.2 |
| 50 | 830.9 | 803.6 | -27.3 | -3.3 | 826.3 | -4.6 | -0.6 |
| 32 | 832.7 | 816.8 | -15.9 | -1.9 | 831.9 | -0.8 | -0.1 |
| 16 | 841.3 | 820.7 | -20.6 | -2.5 | 812.4 | -28.9 | -3.4 |
| 26 | 842.0 | 857.7 | 15.7 | 1.9 | 838.5 | -3.5 | -0.4 |
| 23 | 842.6 | 864.8 | 22.2 | 2.6 | 844.6 | 2.0 | 0.2 |
| 40 | 851.2 | 845.6 | -5.6 | -0.7 | 835.0 | -16.2 | -1.9 |
| 8 | 852.5 | 857.4 | 4.9 | 0.6 | 860.5 | 8.0 | 0.9 |
| 11 | 874.6 | 877.7 | 3.2 | 0.4 | 863.7 | -10.9 | -1.2 |
| 13 | 882.3 | 868.5 | -13.8 | -1.6 | 884.0 | 1.7 | 0.2 |
| 10 | 885.1 | 874.4 | -10.7 | -1.2 | 868.1 | -17.1 | -1.9 |
| 7 | 897.1 | 876.6 | -21.0 | -2.3 | 867.5 | -30.1 | -3.4 |
| 20 | 897.7 | 893.7 | -4.0 | -0.4 | 899.7 | 2.0 | 0.2 |
| 31 | 911.4 | 951.0 | 39.6 | 4.3 | 905.7 | -5.6 | -0.6 |
| 14 | 915.9 | 919.8 | 3.9 | 0.4 | 917.9 | 2.0 | 0.2 |
| 5 | 926.4 | 892.3 | -34.1 | -3.7 | 920.8 | -5.6 | -0.6 |
| 1 | 954.4 | 961.0 | 6.5 | 0.7 | 956.2 | 1.7 | 0.2 |
| 17 | 959.5 | 990.1 | 30.6 | 3.2 | 954.9 | -4.6 | -0.5 |
| 2 | 979.7 | 976.4 | -3.3 | -0.3 | 992.8 | 13.1 | 1.3 |
| 4 | 986.9 | 976.5 | -10.4 | -1.1 | 986.0 | -0.9 | -0.1 |

TABLE 9

| | Z | | mud density not used Model P1 | | | mud density input Model PE | | |
|---|---|---|---|---|---|---|---|---|
| Sample | Actual | Pred. | Error, g/L | Error, % | Pred. | Error, g/L | Error, % |
| 2 | 7.49 | 7.79 | 0.30 | 3.95 | 8.08 | 0.58 | 7.77 |
| 4 | 7.70 | 7.97 | 0.27 | 3.54 | 8.29 | 0.59 | 7.69 |
| 1 | 7.96 | 7.88 | -0.07 | -0.93 | 8.51 | 0.58 | 7.00 |
| 5 | 8.48 | 8.31 | -0.16 | -1.93 | 9.02 | 0.55 | 6.45 |
| 8 | 9.66 | 9.14 | -0.52 | -5.37 | 10.07 | 0.41 | 4.21 |

TABLE 9-continued

| | Z | | mud density not used Model P1 | | | mud density input Model PE | | |
|---|---|---|---|---|---|---|---|---|
| Sample | Actual | Pred. | Error, g/L | Error, % | Pred. | Error, g/L | Error, % |
| 7 | 9.71 | 9.73 | 0.02 | 0.19 | 9.39 | -0.32 | -3.31 |
| 11 | 9.84 | 9.52 | -0.32 | -3.26 | 10.15 | 0.31 | 3.13 |
| 10 | 10.06 | 9.90 | -0.15 | -1.53 | 9.92 | -0.14 | -1.35 |
| 14 | 10.13 | 10.24 | 0.11 | 1.07 | 10.21 | 0.07 | 0.72 |
| 13 | 10.30 | 10.46 | 0.16 | 1.60 | 10.44 | 0.15 | 1.41 |
| 17 | 10.30 | 10.27 | -0.03 | -0.32 | 10.20 | -0.10 | -0.99 |
| 20 | 11.36 | 11.45 | 0.09 | 0.79 | 11.19 | -0.16 | -1.44 |
| 16 | 11.79 | 12.20 | 0.41 | 3.47 | 11.23 | -0.57 | -4.80 |
| 19 | 11.86 | 11.91 | 0.05 | 0.44 | 11.92 | 0.06 | 0.53 |
| 23 | 12.40 | 12.55 | 0.15 | 1.20 | 12.31 | -0.09 | -0.74 |
| 22 | 12.73 | 12.72 | -0.02 | -0.14 | 12.72 | -0.01 | -0.10 |
| 26 | 13.12 | 13.42 | 0.30 | 2.25 | 13.00 | -0.13 | -0.96 |
| 28 | 14.28 | 14.01 | -0.27 | -1.89 | 13.81 | -0.47 | -3.27 |
| 31 | 14.41 | 14.48 | 0.06 | 0.45 | 13.86 | -0.56 | -3.85 |
| 32 | 14.94 | 15.03 | 0.10 | 0.64 | 14.79 | -0.15 | -0.99 |
| 29 | 15.08 | 15.29 | 0.21 | 1.39 | 14.00 | -1.08 | -7.16 |
| 35 | 15.75 | 15.86 | 0.12 | 0.75 | 15.65 | -0.10 | -0.61 |
| 34 | 15.81 | 15.63 | -0.18 | -1.13 | 15.35 | -0.46 | -2.92 |
| 37 | 16.20 | 15.92 | -0.29 | -1.79 | 15.90 | -0.30 | -1.88 |
| 38 | 16.77 | 16.82 | 0.05 | 0.31 | 16.47 | -0.30 | -1.77 |
| 40 | 16.95 | 16.82 | -0.14 | -0.80 | 16.54 | -0.41 | -2.42 |
| 41 | 17.70 | 17.28 | -0.42 | -2.35 | 17.18 | -0.52 | -2.94 |
| 43 | 17.70 | 17.71 | 0.02 | 0.09 | 17.90 | 0.20 | 1.14 |
| 44 | 18.04 | 18.12 | 0.07 | 0.40 | 18.28 | 0.24 | 1.32 |
| 46 | 18.62 | 18.56 | -0.06 | -0.30 | 18.67 | 0.06 | 0.31 |
| 49 | 18.90 | 18.65 | -0.25 | -1.30 | 18.73 | -0.17 | -0.89 |
| 47 | 19.11 | 18.78 | -0.32 | -1.70 | 18.87 | -0.24 | -1.25 |
| 50 | 19.46 | 19.81 | 0.35 | 1.80 | 19.46 | 0.00 | 0.02 |
| 52 | 19.76 | 19.64 | -0.12 | -0.60 | 19.97 | 0.21 | 1.04 |
| 53 | 20.17 | 20.25 | 0.08 | 0.40 | 20.21 | 0.04 | 0.21 |
| 56 | 20.59 | 21.08 | 0.48 | 2.34 | 21.28 | 0.68 | 3.32 |
| 55 | 20.67 | 20.74 | 0.07 | 0.34 | 20.72 | 0.05 | 0.25 |
| 59 | 21.02 | 21.09 | 0.07 | 0.33 | 21.45 | 0.43 | 2.05 |
| 58 | 21.38 | 21.43 | 0.05 | 0.25 | 21.70 | 0.33 | 1.54 |
| 61 | 21.90 | 21.77 | -0.13 | -0.61 | 22.04 | 0.13 | 0.60 |
| 64 | 22.37 | 22.58 | 0.21 | 0.94 | 22.94 | 0.57 | 2.55 |
| 62 | 22.68 | 22.36 | -0.31 | -1.39 | 22.35 | -0.33 | -1.44 |
| 65 | 23.04 | 22.88 | -0.16 | -0.68 | 23.06 | 0.02 | 0.09 |
| 71 | 23.58 | 23.48 | -0.10 | -0.44 | 23.77 | 0.18 | 0.77 |
| 68 | 23.61 | 23.78 | 0.17 | 0.71 | 24.07 | 0.47 | 1.97 |
| 70 | 24.47 | 24.32 | -0.15 | -0.61 | 24.35 | -0.12 | -0.48 |
| 76 | 24.64 | 24.88 | 0.23 | 0.95 | 25.16 | 0.51 | 2.09 |
| 73 | 25.00 | 25.09 | 0.10 | 0.38 | 25.46 | 0.47 | 1.87 |
| 74 | 25.01 | 25.05 | 0.04 | 0.17 | 25.19 | 0.18 | 0.71 |
| 79 | 25.55 | 25.83 | 0.28 | 1.10 | 25.97 | 0.42 | 1.65 |
| 77 | 25.75 | 25.80 | 0.05 | 0.21 | 25.95 | 0.20 | 0.78 |
| 82 | 26.16 | 26.38 | 0.22 | 0.84 | 26.50 | 0.34 | 1.30 |
| 80 | 26.62 | 26.63 | 0.01 | 0.03 | 26.47 | -0.15 | -0.55 |
| 83 | 26.86 | 26.20 | -0.66 | -2.47 | 26.39 | -0.46 | -1.73 |
| 85 | 27.56 | 27.53 | -0.03 | -0.11 | 27.00 | -0.57 | -2.06 |
| 88 | 27.68 | 27.69 | 0.01 | 0.03 | 27.21 | -0.47 | -1.69 |
| 89 | 28.36 | 28.23 | -0.14 | -0.49 | 27.63 | -0.74 | -2.60 |

TABLE 10

| | SG | | Model P2 | |
|---|---|---|---|---|
| Sample | Actual | Pred. | Error, g/L | Error, % |
| 2 | 1.02 | 1.05 | 0.03 | 2.71 |
| 4 | 1.04 | 1.05 | 0.01 | 1.16 |
| 1 | 1.08 | 1.06 | -0.02 | -1.66 |
| 17 | 1.11 | 1.04 | -0.07 | -6.36 |
| 5 | 1.13 | 1.20 | 0.07 | 6.09 |
| 7 | 1.16 | 1.19 | 0.03 | 2.17 |
| 14 | 1.16 | 1.14 | -0.02 | -2.00 |
| 20 | 1.21 | 1.22 | 0.02 | 1.41 |
| 10 | 1.21 | 1.21 | 0.00 | 0.06 |
| 13 | 1.22 | 1.25 | 0.03 | 2.53 |

TABLE 10-continued

SG

| | | Model P2 | | |
|---|---|---|---|---|
| Sample | Actual | Pred. | Error, g/L | Error, % |
| 11 | 1.24 | 1.24 | 0.00 | 0.15 |
| 31 | 1.24 | 1.19 | −0.06 | −4.47 |
| 8 | 1.26 | 1.27 | 0.01 | 0.73 |
| 16 | 1.29 | 1.31 | 0.01 | 1.04 |
| 23 | 1.33 | 1.26 | −0.06 | −4.77 |
| 26 | 1.34 | 1.31 | −0.03 | −2.33 |
| 19 | 1.37 | 1.33 | −0.04 | −2.62 |
| 29 | 1.38 | 1.42 | 0.04 | 2.74 |
| 32 | 1.38 | 1.41 | 0.03 | 1.97 |
| 40 | 1.42 | 1.41 | −0.01 | −0.90 |
| 22 | 1.44 | 1.42 | −0.02 | −1.31 |
| 28 | 1.45 | 1.46 | 0.01 | 0.68 |
| 35 | 1.45 | 1.43 | −0.02 | −1.67 |
| 38 | 1.48 | 1.57 | 0.09 | 5.80 |
| 50 | 1.50 | 1.57 | 0.07 | 4.59 |
| 34 | 1.50 | 1.49 | −0.01 | −0.79 |
| 41 | 1.53 | 1.50 | −0.02 | −1.44 |
| 37 | 1.54 | 1.51 | −0.02 | −1.55 |
| 46 | 1.58 | 1.56 | −0.03 | −1.72 |
| 49 | 1.60 | 1.62 | 0.02 | 1.46 |
| 52 | 1.64 | 1.63 | −0.01 | −0.45 |
| 43 | 1.65 | 1.61 | −0.03 | −2.08 |
| 44 | 1.66 | 1.65 | −0.01 | −0.88 |
| 47 | 1.68 | 1.67 | −0.02 | −0.93 |
| 53 | 1.73 | 1.78 | 0.05 | 2.67 |
| 58 | 1.75 | 1.77 | 0.02 | 1.07 |
| 62 | 1.76 | 1.84 | 0.09 | 4.53 |
| 56 | 1.81 | 1.86 | 0.05 | 2.90 |
| 55 | 1.83 | 1.86 | 0.03 | 1.53 |
| 65 | 1.87 | 1.91 | 0.04 | 2.14 |
| 61 | 1.88 | 1.84 | −0.04 | −2.22 |
| 68 | 1.92 | 1.94 | 0.02 | 1.28 |
| 73 | 1.93 | 1.99 | 0.06 | 3.17 |
| 64 | 1.93 | 1.90 | −0.03 | −1.48 |
| 59 | 1.94 | 1.86 | −0.08 | −4.35 |
| 70 | 1.95 | 1.97 | 0.02 | 1.19 |
| 80 | 2.03 | 2.03 | 0.00 | 0.02 |
| 74 | 2.04 | 2.06 | 0.01 | 0.61 |
| 77 | 2.07 | 2.06 | −0.01 | −0.28 |
| 71 | 2.13 | 2.06 | −0.07 | −3.28 |
| 82 | 2.22 | 2.22 | 0.00 | 0.00 |
| 83 | 2.22 | 2.18 | −0.04 | −1.90 |
| 79 | 2.24 | 2.22 | −0.02 | −0.95 |
| 76 | 2.24 | 2.22 | −0.03 | −1.13 |
| 85 | 2.28 | 2.34 | 0.05 | 2.25 |
| 89 | 2.38 | 2.33 | −0.04 | −1.79 |
| 88 | 2.41 | 2.38 | −0.03 | −1.30 |

TABLE 11

| BARITE | | mud density not used Model PA | | | mud density input Model PE | | |
|---|---|---|---|---|---|---|---|
| Sample | Actual | Pred. | Error, g/L | Error, % | Pred. | Error, g/L | Error, % |
| 9 | 38.3 | 30.9 | −7.4 | −19.3 | 32.8 | −5.5 | −14.3 |
| 12 | 67.3 | 64.1 | −3.2 | −4.8 | 78.9 | 11.6 | 17.3 |
| 18 | 119.5 | 120.5 | 1.0 | 0.8 | 131.4 | 11.9 | 10.0 |
| 21 | 154.4 | 156.4 | 2.0 | 1.3 | 157.1 | 2.7 | 1.7 |
| 24 | 183.7 | 177.3 | −6.5 | −3.5 | 185.2 | 1.4 | 0.8 |
| 27 | 226.6 | 234.7 | 8.1 | 3.6 | 231.1 | 4.4 | 2.0 |
| 30 | 273.2 | 257.5 | −15.8 | −5.8 | 264.4 | −8.9 | −3.2 |
| 33 | 323.8 | 341.5 | 17.7 | 5.5 | 330.7 | 6.8 | 2.1 |
| 36 | 373.8 | 380.6 | 6.8 | 1.8 | 347.3 | −26.5 | −7.1 |
| 39 | 424.8 | 446.6 | 21.8 | 5.1 | 443.6 | 18.8 | 4.4 |
| 42 | 467.0 | 472.5 | 5.5 | 1.2 | 469.8 | 2.8 | 0.6 |
| 48 | 559.2 | 557.9 | −1.4 | −0.2 | 563.3 | 4.1 | 0.7 |
| 51 | 615.5 | 647.7 | 32.1 | 5.2 | 629.2 | 13.7 | 2.2 |
| 54 | 678.5 | 681.3 | 2.8 | 0.4 | 694.3 | 15.8 | 2.3 |
| 57 | 741.0 | 759.6 | 18.7 | 2.5 | 759.8 | 18.8 | 2.5 |
| 60 | 797.0 | 783.1 | −13.9 | −1.7 | 776.5 | −20.6 | −2.6 |
| 63 | 867.7 | 883.3 | 15.6 | 1.8 | 876.7 | 9.0 | 1.0 |
| 66 | 930.1 | 943.9 | 13.8 | 1.5 | 925.5 | −4.6 | −0.5 |
| 69 | 1000.9 | 1035.7 | 34.8 | 3.5 | 1016.5 | 15.6 | 1.6 |
| 72 | 1076.9 | 1083.9 | 7.0 | 0.6 | 1070.5 | −6.4 | −0.6 |
| 75 | 1152.5 | 1188.6 | 36.1 | 3.1 | 1165.3 | 12.8 | 1.1 |
| 78 | 1231.1 | 1257.2 | 26.1 | 2.1 | 1230.0 | −1.1 | −0.1 |
| 81 | 1298.0 | 1300.0 | 2.0 | 0.2 | 1315.1 | 17.1 | 1.3 |
| 84 | 1385.5 | 1336.9 | −48.6 | −3.5 | 1389.7 | 4.2 | 0.3 |
| 87 | 1495.1 | 1449.2 | −45.9 | −3.1 | 1513.0 | 17.9 | 1.2 |

TABLE 12

| CALCIUM | | mud density not used Model PR01 | | | mud density input Model PG | | |
|---|---|---|---|---|---|---|---|
| Sample | Actual | Pred. | Error, g/L | Error, % | Pred. | Error, g/L | Error, % |
| 39 | 3.0 | 5.1 | 2.1 | 69.4 | 8.0 | 4.9 | 162.6 |
| 24 | 3.2 | −13.5 | −16.7 | −526.1 | 6.5 | 3.4 | 106.7 |
| 81 | 3.3 | 14.8 | 11.5 | 345.0 | 20.6 | 17.2 | 518.1 |
| 9 | 6.9 | 9.1 | 2.1 | 30.9 | 6.4 | −0.5 | −7.2 |
| 30 | 8.2 | −5.1 | −13.3 | −162.8 | 7.3 | −0.9 | −10.9 |
| 48 | 11.8 | 26.6 | 14.8 | 125.2 | 30.3 | 18.4 | 155.9 |
| 36 | 17.0 | 16.6 | −0.4 | −2.2 | 16.3 | −0.7 | −4.0 |
| 69 | 30.5 | 32.8 | 2.3 | 7.5 | 22.6 | −7.9 | −26.0 |
| 66 | 34.1 | 36.6 | 2.5 | 7.3 | 23.6 | −10.5 | −30.8 |
| 78 | 38.6 | 42.9 | 4.3 | 11.1 | 21.9 | −16.7 | −43.3 |
| 42 | 39.4 | 34.3 | −5.0 | −12.8 | 35.7 | −3.6 | −9.2 |
| 21 | 43.7 | 21.9 | −21.8 | −49.8 | 32.6 | −11.1 | −25.4 |
| 12 | 49.4 | 26.2 | −23.2 | −47.0 | 39.6 | −9.8 | −19.8 |
| 51 | 50.7 | 57.9 | 7.2 | 14.2 | 45.5 | −5.2 | −10.3 |
| 87 | 51.4 | 56.2 | 4.8 | 9.4 | 65.6 | 14.2 | 27.6 |
| 84 | 60.8 | 67.0 | 6.2 | 10.2 | 81.5 | 20.7 | 34.0 |
| 60 | 63.9 | 62.0 | −1.9 | −3.0 | 55.9 | −8.0 | −12.5 |
| 75 | 70.5 | 71.8 | 1.2 | 1.8 | 69.1 | −1.4 | −2.0 |
| 57 | 75.0 | 76.4 | 1.5 | 2.0 | 70.8 | −4.1 | −5.5 |
| 72 | 82.5 | 90.9 | 8.4 | 10.1 | 85.3 | 2.8 | 3.4 |
| 33 | 85.7 | 79.3 | −6.5 | −7.5 | 72.3 | −13.4 | −15.6 |
| 18 | 94.3 | 63.6 | −30.7 | −32.6 | 80.8 | −13.5 | −14.3 |
| 54 | 97.2 | 92.4 | −4.8 | −4.9 | 90.6 | −6.6 | −6.8 |
| 27 | 99.4 | 75.4 | −24.0 | −24.1 | 78.7 | −20.7 | −20.8 |
| 63 | 101.7 | 97.4 | −4.3 | −4.3 | 97.5 | −4.2 | −4.2 |

TABLE 13

| POTAS-SIUM | | mud density not used Model PR01 | | | mud density input Model PG | | |
|---|---|---|---|---|---|---|---|
| Sample | Actual | Pred. | Error, g/L | Error, % | Pred. | Error, g/L | Error, % |
| 51 | 1.0 | 4.4 | 3.3 | 333.9 | 2.0 | 1.0 | 100.5 |
| 42 | 1.4 | 3.5 | 2.1 | 154.7 | 0.6 | −0.8 | −56.9 |
| 9 | 1.5 | −1.1 | −2.6 | −172.1 | −4.3 | −5.8 | −384.5 |
| 66 | 1.6 | 3.4 | 1.8 | 110.3 | 4.8 | 3.2 | 197.4 |
| 69 | 2.3 | 5.3 | 3.0 | 131.0 | 6.7 | 4.4 | 192.9 |
| 36 | 3.0 | −5.1 | −8.2 | −269.1 | 1.2 | −1.8 | −59.7 |
| 57 | 4.1 | 10.5 | 6.4 | 154.7 | 9.0 | 4.9 | 118.5 |
| 60 | 4.4 | 4.5 | 0.1 | 1.7 | 9.6 | 5.2 | 118.2 |
| 78 | 4.8 | −0.5 | −5.3 | −110.5 | 11.3 | 6.5 | 136.1 |
| 21 | 5.3 | 1.4 | −3.9 | −74.4 | 0.0 | −5.3 | −100.7 |
| 30 | 8.8 | 2.6 | −6.2 | −70.5 | 8.1 | −0.7 | −8.0 |
| 81 | 9.8 | 15.4 | 5.6 | 57.2 | 15.9 | 6.1 | 62.9 |
| 54 | 11.0 | 13.2 | 2.3 | 20.6 | 14.9 | 4.0 | 36.0 |
| 18 | 18.1 | 17.7 | −0.4 | −2.0 | 13.6 | −4.5 | −24.8 |
| 39 | 22.6 | 22.5 | −0.1 | −0.7 | 24.2 | 1.5 | 6.8 |
| 12 | 24.9 | 16.9 | −8.0 | −32.1 | 20.9 | −3.9 | −15.9 |
| 33 | 30.6 | 26.4 | −4.2 | −13.6 | 25.8 | −4.8 | −15.6 |

TABLE 13-continued

| POTAS-SIUM | | mud density not used Model PR01 | | | mud density input Model PG | | |
|---|---|---|---|---|---|---|---|
| Sample | Actual | Pred. | Error, g/L | Error, % | Pred. | Error, g/L | Error, % |
| 24 | 33.3 | 36.8 | 3.5 | 10.6 | 39.4 | 6.1 | 18.4 |
| 75 | 38.3 | 41.6 | 3.4 | 8.8 | 34.9 | −3.3 | −8.7 |
| 87 | 39.6 | 32.7 | −6.9 | −17.5 | 40.7 | 1.1 | 2.8 |
| 48 | 56.0 | 58.0 | 2.0 | 3.6 | 56.0 | 0.0 | 0.1 |
| 84 | 58.0 | 53.9 | −4.1 | −7.1 | 53.1 | −4.9 | −8.5 |
| 27 | 77.8 | 77.8 | 0.0 | −0.1 | 80.8 | 3.0 | 3.9 |
| 72 | 88.0 | 72.1 | −15.9 | −18.1 | 69.0 | −19.0 | −21.6 |
| 63 | 93.1 | 70.1 | −23.0 | −24.7 | 67.1 | −26.0 | −27.9 |

TABLE 14

| CHLORIDE | | mud density not used Model P2 | | | mud density input Model PG | | |
|---|---|---|---|---|---|---|---|
| Sample | Actual | Pred. | Error, g/L | Error, % | Pred. | Error, g/L | Error, % |
| 9 | 2.5 | −1.6 | −4.1 | −162.7 | −6.5 | −9.0 | −361.3 |
| 51 | 3.2 | 15.6 | 12.4 | 395.0 | 9.7 | 6.5 | 206.3 |
| 42 | 4.4 | 9.1 | 4.7 | 106.3 | 7.6 | 3.2 | 71.6 |
| 60 | 8.2 | 14.9 | 6.7 | 81.3 | 21.4 | 13.1 | 159.4 |
| 78 | 8.7 | 19.3 | 10.6 | 122.2 | 19.6 | 10.9 | 125.6 |
| 66 | 15.6 | 28.2 | 12.6 | 80.4 | 23.3 | 7.6 | 48.9 |
| 69 | 49.9 | 54.0 | 4.1 | 8.2 | 50.5 | 0.6 | 1.2 |
| 39 | 61.0 | 61.3 | 0.3 | 0.5 | 66.9 | 5.9 | 9.6 |
| 48 | 70.1 | 81.2 | 11.1 | 15.8 | 78.2 | 8.1 | 11.5 |
| 24 | 74.0 | 73.5 | −0.5 | −0.6 | 86.5 | 12.5 | 16.9 |
| 84 | 76.6 | 86.2 | 9.6 | 12.6 | 92.1 | 15.5 | 20.3 |
| 30 | 78.3 | 74.0 | −4.2 | −5.4 | 88.2 | 9.9 | 12.7 |
| 36 | 80.0 | 76.3 | −3.6 | −4.5 | 86.4 | 6.5 | 8.1 |
| 87 | 85.2 | 81.5 | −3.7 | −4.4 | 90.1 | 4.9 | 5.7 |
| 27 | 92.6 | 96.4 | 3.8 | 4.1 | 101.2 | 8.6 | 9.3 |
| 18 | 109.0 | 106.6 | −2.4 | −2.2 | 106.4 | −2.6 | −2.4 |
| 57 | 111.0 | 109.3 | −1.6 | −1.5 | 105.8 | −5.2 | −4.7 |
| 72 | 111.8 | 116.6 | 4.8 | 4.3 | 111.9 | 0.1 | 0.1 |
| 75 | 114.5 | 113.3 | −1.2 | −1.0 | 105.8 | −8.8 | −7.7 |
| 12 | 117.3 | 105.1 | −12.2 | −10.4 | 114.8 | −2.5 | −2.1 |
| 33 | 130.9 | 130.6 | −0.4 | −0.3 | 126.1 | −4.8 | −3.7 |
| 63 | 136.1 | 126.3 | −9.8 | −7.2 | 125.9 | −10.3 | −7.5 |
| 54 | 141.9 | 128.8 | −13.0 | −9.2 | 131.5 | −10.4 | −7.3 |
| 21 | 144.2 | 143.4 | −0.8 | −0.5 | 143.7 | −0.4 | −0.3 |
| 81 | 148.8 | 104.4 | −44.4 | −29.8 | 105.5 | −43.2 | −29.1 |

TABLE 15

| LGS | | mud density not used Model P2 | | | mud density input Model PG | | |
|---|---|---|---|---|---|---|---|
| Sample | Actual | Pred. | Error, g/L | Error, % | Pred. | Error, g/L | Error, % |
| 9 | 37.7 | 25.3 | −12.4 | −32.9 | 52.8 | 15.1 | 40.2 |
| 24 | 188.6 | 103.4 | −85.2 | −45.2 | 157.9 | −30.7 | −16.3 |
| 30 | 196.8 | 152.5 | −44.4 | −22.5 | 209.6 | 12.7 | −6.5 |
| 12 | 224.6 | 128.5 | −96.1 | −42.8 | 169.8 | −54.7 | −24.4 |
| 21 | 238.5 | 210.1 | −28.1 | −11.8 | 220.9 | −17.4 | −7.3 |
| 36 | 243.4 | 258.7 | 15.3 | 6.3 | 266.9 | 23.5 | 9.7 |
| 39 | 262.3 | 252.9 | −9.4 | −3.6 | 266.2 | 3.9 | 1.5 |
| 42 | 263.7 | 282.0 | 18.3 | 6.9 | 293.5 | 29.8 | 11.3 |
| 27 | 263.8 | 225.2 | −38.6 | −14.6 | 276.1 | 12.3 | 4.7 |
| 18 | 297.1 | 211.3 | −85.8 | −28.9 | 259.6 | −37.5 | −12.6 |
| 33 | 336.0 | 361.5 | 25.5 | 7.6 | 351.0 | 15.0 | 4.5 |
| 51 | 340.4 | 418.3 | 77.9 | 22.9 | 363.9 | 23.5 | 6.9 |
| 48 | 389.6 | 339.4 | −50.1 | −12.9 | 349.5 | −40.1 | −10.3 |
| 60 | 443.5 | 470.6 | 27.0 | 6.1 | 448.2 | 4.7 | 1.1 |
| 66 | 454.1 | 502.3 | 48.2 | 10.6 | 446.7 | −7.4 | −1.6 |
| 69 | 501.1 | 537.6 | 36.5 | 7.3 | 494.0 | −7.0 | −1.4 |
| 57 | 503.2 | 534.0 | 30.8 | 6.1 | 517.6 | 14.5 | 2.9 |
| 54 | 541.6 | 535.7 | −5.9 | −1.1 | 546.7 | 5.0 | 0.9 |
| 63 | 550.4 | 603.8 | 53.3 | 9.7 | 605.4 | 55.0 | 10.0 |

TABLE 15-continued

| LGS | | mud density not used Model P2 | | | mud density input Model PG | | |
|---|---|---|---|---|---|---|---|
| Sample | Actual | Pred. | Error, g/L | Error, % | Pred. | Error, g/L | Error, % |
| 78 | 585.2 | 613.3 | 28.1 | 4.8 | 550.0 | −35.2 | −6.0 |
| 72 | 595.0 | 657.1 | 62.1 | 10.4 | 648.6 | 53.6 | 9.0 |
| 75 | 639.1 | 680.8 | 41.7 | 6.5 | 662.8 | 23.6 | 3.7 |
| 81 | 658.6 | 627.5 | −31.1 | −4.7 | 649.7 | −8.9 | −1.3 |
| 84 | 810.3 | 720.1 | −90.2 | −11.1 | 784.3 | −26.0 | −3.2 |
| 87 | 817.7 | 723.1 | −94.6 | −11.6 | 795.0 | −22.7 | −2.8 |

TABLE 16

| WATER | | mud density not used Model P2 | | | mud density input Model PG | | |
|---|---|---|---|---|---|---|---|
| Sample | Actual | Pred. | Error, g/L | Error, % | Pred. | Error, g/L | Error, % |
| 87 | 510.9 | 544.8 | 34.0 | 6.7 | 502.9 | −8.0 | −1.6 |
| 84 | 514.1 | 538.5 | 24.4 | 4.7 | 505.3 | −8.8 | −1.7 |
| 75 | 584.7 | 560.5 | −24.2 | −4.1 | 578.4 | −6.3 | −1.1 |
| 72 | 587.1 | 554.6 | −32.5 | −5.5 | 567.1 | −20.0 | −3.4 |
| 81 | 590.1 | 607.9 | 17.7 | 3.0 | 594.0 | 3.9 | 0.7 |
| 63 | 595.2 | 586.5 | −8.7 | −1.5 | 590.3 | −4.9 | −0.8 |
| 54 | 651.9 | 658.6 | 6.8 | 1.0 | 653.9 | 2.1 | 0.3 |
| 78 | 671.6 | 647.7 | −24.0 | −3.6 | 671.9 | 0.3 | 0.0 |
| 57 | 690.7 | 665.9 | −24.9 | −3.6 | 678.8 | −11.9 | −1.7 |
| 69 | 709.6 | 681.4 | −28.2 | −4.0 | 702.3 | −7.3 | −1.0 |
| 66 | 738.3 | 710.4 | −27.9 | −3.8 | 738.0 | −0.2 | 0.0 |
| 60 | 743.4 | 735.4 | −8.0 | −1.1 | 737.8 | −5.6 | −0.8 |
| 33 | 748.7 | 744.8 | −3.9 | −0.5 | 754.9 | 6.2 | 0.8 |
| 48 | 752.5 | 755.6 | 3.1 | 0.4 | 755.0 | 2.5 | 0.3 |
| 27 | 776.2 | 796.5 | 20.3 | 2.6 | 767.3 | −8.9 | −1.1 |
| 18 | 787.6 | 837.4 | 49.8 | 6.3 | 813.8 | 26.2 | 3.3 |
| 51 | 809.2 | 763.2 | −46.0 | −5.7 | 792.9 | −16.3 | −2.0 |
| 21 | 817.0 | 844.7 | 27.8 | 3.4 | 836.9 | 19.9 | 2.4 |
| 39 | 835.0 | 836.8 | 1.8 | 0.2 | 823.3 | −11.7 | −1.4 |
| 12 | 837.0 | 891.5 | 54.4 | 6.5 | 859.7 | 22.7 | 2.7 |
| 36 | 846.6 | 846.9 | 0.3 | 0.0 | 830.6 | −16.1 | −1.9 |
| 42 | 850.6 | 841.2 | −9.4 | −1.1 | 835.7 | −14.9 | −1.8 |
| 24 | 869.1 | 909.0 | 39.9 | 4.6 | 868.7 | −0.4 | 0.0 |
| 30 | 875.5 | 902.0 | 26.5 | 3.0 | 858.7 | −16.8 | −1.9 |
| 9 | 874.3 | 986.2 | 11.9 | 1.2 | 981.0 | 6.6 | 0.7 |

TABLE 17

| Z | | mud density not used Model P1 | | | mud density input Model PE | | |
|---|---|---|---|---|---|---|---|
| Sample | Actual | Pred. | Error, g/L | Error, % | Pred. | Error, g/L | Error, % |
| 9 | 8.40 | 8.50 | 0.10 | 1.14 | 8.72 | 0.31 | 3.72 |
| 12 | 10.61 | 10.15 | −0.46 | −4.33 | 10.74 | 0.13 | 1.23 |
| 18 | 11.85 | 11.75 | −0.10 | −0.87 | 11.91 | 0.06 | 0.50 |
| 21 | 12.46 | 12.60 | 0.13 | 1.08 | 12.22 | −0.24 | −1.93 |
| 24 | 12.60 | 12.60 | 0.00 | 0.01 | 12.45 | −0.15 | −1.17 |
| 27 | 14.15 | 14.61 | 0.46 | 3.25 | 13.72 | −0.43 | −3.02 |
| 30 | 14.29 | 14.27 | −0.02 | −0.11 | 13.91 | −0.38 | −2.64 |
| 33 | 15.63 | 15.88 | 0.26 | 1.66 | 15.44 | −0.18 | −1.16 |
| 36 | 16.10 | 16.61 | 0.51 | 3.18 | 15.85 | −0.25 | −1.55 |
| 39 | 16.92 | 17.40 | 0.48 | 2.83 | 16.93 | 0.01 | 0.04 |
| 42 | 17.48 | 17.71 | 0.23 | 1.29 | 17.95 | 0.47 | 2.67 |
| 48 | 18.82 | 18.88 | 0.06 | 0.31 | 18.92 | 0.10 | 0.54 |
| 51 | 19.60 | 19.88 | 0.28 | 1.43 | 19.74 | 0.14 | 0.71 |
| 54 | 20.12 | 19.97 | −0.14 | −0.72 | 20.60 | 0.48 | 2.38 |
| 57 | 20.91 | 20.86 | −0.05 | −0.25 | 21.47 | 0.56 | 2.66 |
| 60 | 21.79 | 21.70 | −0.10 | −0.45 | 21.73 | −0.07 | −0.31 |
| 63 | 22.48 | 22.44 | −0.04 | −0.20 | 22.55 | 0.07 | 0.31 |
| 66 | 23.42 | 23.37 | −0.05 | −0.21 | 23.45 | 0.04 | 0.15 |
| 69 | 23.99 | 24.29 | 0.30 | 1.24 | 24.38 | 0.39 | 1.61 |
| 72 | 24.46 | 24.40 | −0.06 | −0.23 | 24.39 | −0.07 | −0.27 |
| 75 | 25.05 | 25.39 | 0.34 | 1.36 | 25.30 | 0.25 | 1.00 |

TABLE 17-continued

| | Z | | mud density not used Model P1 | | mud density input Model PE | | |
|---|---|---|---|---|---|---|---|
| Sample | Actual | Pred. | Error, g/L | Error, % | Pred. | Error, g/L | Error, % |
| 78 | 26.06 | 26.56 | 0.50 | 1.91 | 26.26 | 0.20 | 0.76 |
| 81 | 26.38 | 26.64 | 0.25 | 0.95 | 26.59 | 0.20 | 0.76 |
| 84 | 26.42 | 26.57 | 0.15 | 0.57 | 26.42 | 0.00 | −0.01 |
| 87 | 27.34 | 27.49 | 0.15 | 0.53 | 27.24 | −0.10 | −0.36 |

TABLE 18

| | SG | | | |
|---|---|---|---|---|
| | | Model P2 | | |
| Sample | Actual | Pred. | Error, g/L | Error, % |
| 9 | 1.05 | 1.03 | −0.01 | −1.16 |
| 24 | 1.28 | 1.20 | −0.08 | −6.25 |
| 12 | 1.29 | 1.18 | −0.11 | −8.40 |
| 30 | 1.33 | 1.25 | −0.08 | −5.74 |
| 21 | 1.34 | 1.31 | −0.03 | −2.45 |
| 18 | 1.38 | 1.30 | −0.07 | −5.18 |
| 36 | 1.41 | 1.40 | −0.01 | −0.73 |
| 39 | 1.43 | 1.43 | 0.00 | −0.14 |
| 42 | 1.43 | 1.44 | 0.00 | 0.32 |
| 27 | 1.44 | 1.40 | −0.05 | −3.31 |
| 33 | 1.52 | 1.55 | 0.03 | 1.83 |
| 51 | 1.57 | 1.65 | 0.08 | 5.00 |
| 48 | 1.61 | 1.59 | −0.02 | −1.24 |
| 60 | 1.73 | 1.75 | 0.02 | 0.93 |
| 66 | 1.79 | 1.85 | 0.05 | 3.02 |
| 57 | 1.82 | 1.84 | 0.02 | 1.34 |
| 54 | 1.84 | 1.83 | −0.02 | −0.82 |
| 69 | 1.88 | 1.93 | 0.05 | 2.48 |
| 63 | 1.99 | 1.99 | 0.01 | 0.34 |
| 78 | 2.03 | 2.07 | 0.04 | 1.83 |
| 72 | 2.10 | 2.11 | 0.02 | 0.74 |
| 75 | 2.13 | 2.16 | 0.03 | 1.57 |
| 81 | 2.17 | 2.14 | −0.03 | −1.51 |
| 84 | 2.34 | 2.25 | −0.09 | −3.76 |
| 87 | 2.38 | 2.29 | −0.10 | −4.01 |

We claim:

1. A method of analyzing a drilling fluid comprising solids suspended in a liquid phase, the method comprising subjecting a sample of the fluid to an X-ray fluorescence (XRF) analysis technique so as to derive a spectrum therefrom; analyzing the spectrum to identify a peak of intensity $I_{HGS}$ in the spectrum due to the presence of a component of the high gravity solids fraction of the sample and a peak of intensity $I_{Co}$ due to Compton scattering and determining the ratio $I_{HGS}/I_{Co}$; and using data from the derived spectrum, the ratio $I_{HGS}/I_{Co}$ and a calibration model to calculate the amount of said component and liquid phase in the sample.

2. A method as claimed in claim 1, further including the step of calculating the specific gravity SG of the sample.

3. A method as claimed in claim 1, comprising measuring the SG of the sample and using the measured SG in the calculation.

4. A method as claimed in any preceding claim, comprising calculating the amount of low gravity solids in the sample.

5. A method as claimed in any of claims 1–3, comprising calculating the average atomic number Z of the sample.

6. A method as claimed in claim 4, comprising measuring the amounts of salts in the sample and using the measured amount to calculate the amount of low gravity solids in the sample.

7. A method as claimed in any of claims 1–3, wherein the sample is irradiated from a single source.

8. A method as claimed in any of claims 1–3, wherein the component of the high gravity solids fraction contains barium.

9. A method as claimed in any of claims 1–3, wherein the sample is irradiated from two different sources.

10. A method as claimed in claim 9; wherein the spectrum produced by irradiation with a first source is used to calculate the amount of said component of the high gravity solids fraction of the sample which in turn is used together with the spectrum from a second source to calculate the amount of other components in the sample.

11. A method as claimed in any of claims 1–3, wherein the liquid phase is water.

12. A method as claimed in any of claims 1–3, wherein the drilling fluid is oil-based, the liquid phase comprising oil and brine.

13. A method of analyzing the concentration of one or more polymers in a drilling fluid comprising obtaining the IR spectrum of the sample, subjecting the sample to XRF analysis by a method as claimed in any of claims 1–3, to determine the concentration of minerals in the sample, comparing the IR spectrum with a calibration model corrected with the results of the XRF analysis to determine the concentration of polymers in the sample.

14. A method as claimed in any of claims 1–3, wherein the calibration model is constructed from analysis of various fluids of known composition.

15. A method as claimed in any of claims 1–3, which utilizes a regression technique to relate the measurements to the calibration model.

16. A method as claimed in claim 15, wherein the regression technique is a partial least squares method.

17. A method as claimed in any of claims 1–3, wherein the XRF technique provides spectral information of sulfur, chlorine, potassium, chromium and barium in the sample.

18. A method as claimed in claim 9, wherein the sources are Am 241 and Fe 55.

19. A method as claimed in any of claims 1–3 including determining calcium concentration, density and optionally oil/water volume ratio.

20. A method as claimed in claim 19, wherein calcium concentration is determined by EDTA titration or by use of an ion-selective electrode.

21. A method as claimed in claim 20, wherein the sample is analyzed to give barite content, LGS not containing Ca, LGS containing Ca, soluble K, Cl, water content and oil content.

22. A method as claimed in claim 10, wherein the first source is used to give an approximate determination of the Ba content of the fluid which is then used in the analysis of the second source for Ba and other fluid components and physical properties, at least one of the physical properties determined from the second source being used in a further analysis of the first source response to improve the determination of Ba.

23. A method as claimed in claim 12, wherein the density of the brine is also calculated.

24. A method as claimed in claim 12, wherein the water activity of the brine is also calculated.

25. A method as claimed in claim 23, wherein the water activity of the brine is also calculated.

* * * * *